(12) United States Patent
Lowe, III

(10) Patent No.: US 6,566,550 B2
(45) Date of Patent: May 20, 2003

(54) SUBSTITUTED AROMATIC ETHERS AS INHIBITORS OF GLYCINE TRANSPORT

(75) Inventor: John A. Lowe, III, Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/086,037

(22) Filed: Feb. 28, 2002

(65) Prior Publication Data

US 2003/0013887 A1 Jan. 16, 2003

Related U.S. Application Data

(60) Provisional application No. 60/299,827, filed on Jun. 21, 2001.

(51) Int. Cl.$^7$ ..................... C07C 229/28; A61K 31/195
(52) U.S. Cl. ................... 562/451; 562/443; 514/567
(58) Field of Search ................ 562/451, 443; 514/567

(56) References Cited

U.S. PATENT DOCUMENTS 6,191,165 B1 * 2/2001 Ognyanov et al. ......... 514/523
2002/0052401 A1   5/2002 Lowe, III .................. 514/438

FOREIGN PATENT DOCUMENTS

WO    WO9745115    12/1997 .......... A61K/31/34

OTHER PUBLICATIONS

Richard Bergeron et al., Proc. Natl. Acad. Sci. USA, vol. 95, pp. 1530–1573, Dec. 1998, Neurobiology, "Modulation of N–methyl–D–aspartate receptor function by glycine transport."

Angus Brown et al, Bioorganic & Medicinal Chemistry Letters 11 (2001) 2007–2009, "Discovery and SAR of Org 24598—A Seclective Glycine Uptake Inhibitor."

H. J. Herdone et al., Neuropharmacology 41 (2001) 88–96, "Pharmacological assessment of the role of the glycine transporter GlyT–1 in mediating high–affinity glycine uptake by rat cerebral cortex and cerebellum synaptosomes."

* cited by examiner

Primary Examiner—Shailendra Kumar
(74) Attorney, Agent, or Firm—Peter C. Richardson; Paul H. Ginsburg; Krishna G. Banerjee

(57) ABSTRACT

This invention relates to a series of substituted aromatic ethers of the formula I

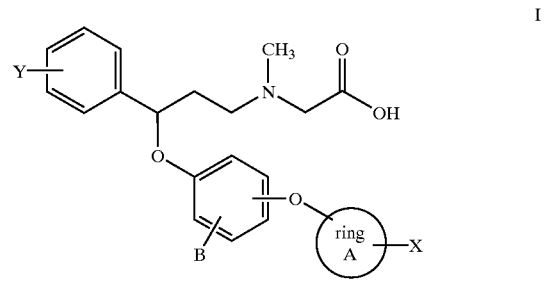

wherein ring A and X and Y are defined as in the specification, that exhibit activity as glycine transport inhibitors, their pharmaceutically acceptable salts, pharmaceutical compositions containing them, and their use for the enhancement of cognition and the treatment of the positive and negative symptoms of schizophrenia and other psychoses in mammals, including humans.

10 Claims, No Drawings

SUBSTITUTED AROMATIC ETHERS AS INHIBITORS OF GLYCINE TRANSPORT

This application claims the benefit of U.S. Ser. No. 60/299,827, filed Jun. 21, 2001, the contents of which are incorporated herein by reference.

BACKGROUND

The present invention relates to aromatic ethers containing a pendant amino acid side chain and to pharmaceutical compositions containing them and to their use in the treatment of central nervous system disorders, cognitive disorders, schizophrenia, dementia and other disorders in mammals, including humans. These compounds exhibit activity as inhibitors of the glycine type-1 transporter.

Schizophrenia, a progressive neurological disease, is manifested in its early stages as thought disorders such as hallucinations, paranoid delusions, and bizarre thought patterns, collectively known as positive symptoms. These easily recognizable symptoms gave the disease the historical name "madness". As the disease progresses, negative symptoms, such as social withdrawal and anhedonia, and cognitive symptoms such as dementia become more apparent. Only about one-third of schizophrenic patients can be treated successfully and returned to society, while the remainder are generally institutionalized. The burden on society of this devastating illness and the toll it takes on family members of affected patients make it one of the most costly of all CNS diseases.

Pharmacological treatment for schizophrenia has traditionally involved blockade of the dopamine system, which is thought to be responsible for its positive symptoms. Such treatment, however, ignores the negative and cognitive aspects of the disease. Another neurotransmitter system believed to play a role in schizophrenia is the glutamate system, the major excitatory transmitter system in the brain. This hypothesis is based on the observation that blockade of the glutamate system by compounds such as PCP ("angel dust") can replicate many of the symptoms of schizophrenia, including its positive, negative, and cognitive aspects. If schizophrenia involves a deficit of glutamatergic transmission, augmentation of the glutamate system, and specifically the NMDA receptor, may be beneficial. While glutamate is the principle agonist at NMDA receptors, glycine is required as a co-agonist to set the "tone" of the receptor for its response to glutamate. Enhancing this "tone" by increasing the effect of glycine would augment NMDA neurotransmission, and provide potential benefit in the treatment of schizophrenia.

A specific mechanism for augmenting the glycinergic "tone" of the NMDA receptor was disclosed recently by Bergeron, et al. (*Proc. Natl. Acad. Sci. USA*, 95, 15730, (1998)). This group showed that a specific and potent inhibitor of the glycine type-1 transporter (GlyT1) responsible for removing glycine from the synapse at the NMDA receptor, termed NFPS (WO 97/45115), can enhance NMDA receptor function. For example, NFPS increased the post synaptic current driven by the NMDA receptor, an effect blocked by both a specific NMDA-site antagonist and a glycine-site antagonist. Even though glycine levels in the brain are high relative to the amount required to act as an NMDA receptor co-agonist, this work shows that GlyT1 removes glycine efficiently at the synapse, and that inhibition of GlyT1 can augment NMDA receptor function. The authors establish the feasibility of using a GlyT1 inhibitor as a treatment for schizophrenia through augmentation of glutamatergic neurotransmission.

SUMMARY OF THE INVENTION

The present invention relates to a series of substituted aromatic ethers of the formula

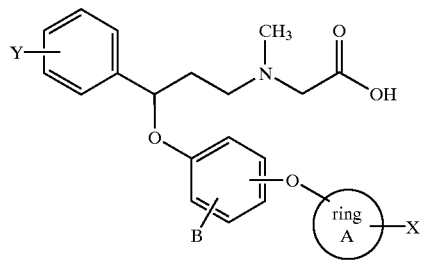

I wherein
ring A is phenyl, naphthyl, benzothienyl, benzofuranyl, or pyridyl; or ring A is a monocyclic aryl or heteroaryl ring containing from zero to four heteroatoms and not containing any adjacent ring oxygen atoms; or ring A is a bicyclic aryl or heteroaryl ring containing from zero to five heteroatoms and not containing any adjacent ring oxygen atoms; and X and Y are each, independently, $(C_1-C_6)$ alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$ alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di[$(C_1-C_6)$ alkyl]amino;

B is $(C_1-C_6)$alkyl, $(C_1-C_6)$alkoxy optionally substituted with 1 to 7 fluorine atoms, or halogen;

and the pharmaceutically acceptable salts of such compounds.

In a preferred embodiment of this invention, ring A is selected from phenyl, naphthyl benzofuranyl, benzothienyl, indanyl, tetrahydronaphthyl, dihydrobenzofuranyl, and dihydrobenzothiophenyl. In another preferred embodiment of this invention, X is para-trifluoromethyl, para-methyl or para-chloro.

The present invention also relates to a compound having the formula:

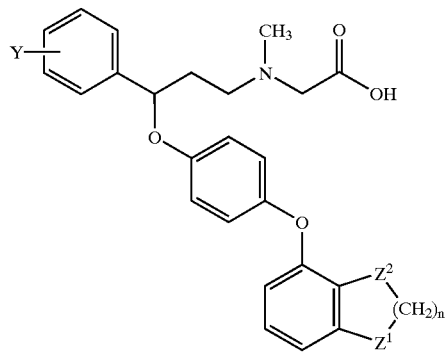

wherein Y is $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing ($C_1$–$C_6$)alkyl and ($C_1$–$C_6$) alkoxy groups can not exceed the number of positions in such groups that are available for substitution; carboxy; carbo-($C_1$–$C_6$)alkoxy; carboxamido; ($C_1$–$C_6$)alkyl-thio; sulfoxyl; sulfonyl; halo; nitro; cyano; amino; ($C_1$–$C_6$) alkylamino and di{($C_1$–$C_6$)alkyl}amino;

wherein $Z^1$ and $Z^2$ are independently selected from O, NH, N—($C_1$–$C_5$ alkyl), and S; and n is an integer from 1 to about 3;

or a pharmaceutically acceptable salt thereof.

The present invention also relates to a compound having the formula:

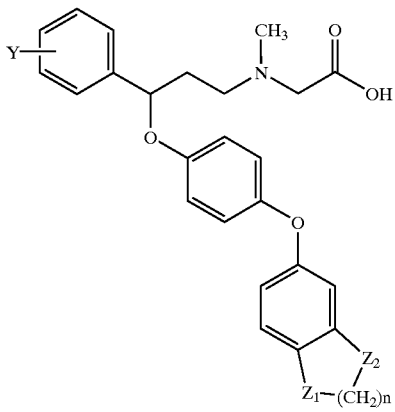

wherein Y is ($C_1$–$C_6$)alkyl optionally substituted with from one to seven fluorine atoms; ($C_1$–$C_6$)alkoxy optionally substituted with from one to seven fluorine atoms, wherein the number of fluorine substituents on the foregoing ($C_1$–$C_6$)alkyl and ($C_1$–$C_6$) alkoxy groups can not exceed the number of positions in such groups that are available for substitution; carboxy; carbo-($C_1$–$C_6$)alkoxy; carboxamido; ($C_1$–$C_6$)alkyl-thio; sulfoxyl; sulfonyl; halo; nitro; cyano; amino; ($C_1$–$C_6$) alkylamino and di{($C_1$–$C_6$)alkyl}amino;

wherein $Z^1$ and $Z^2$ are independently selected from O, NH, N—($C_1$–$C_5$ alkyl), and S; and n is an integer from 1 to about 3;

or a pharmaceutically acceptable salt thereof.

Specific preferred embodiments of the invention include:
{Methyl-[3-(4-phenoxy-phenoxy)-3-phenyl-propyl]-amino}-acetic acid
(Methyl-{3-phenyl-3-[4-(4-trifluoromethyl-phenoxy)-phenoxy]-propyl}-amino)-acetic acid
(Methyl-{3-phenyl-3-[4-(3-trifluoromethyl-phenoxy)-phenoxy]-propyl}-amino)-acetic acid
{Methyl-[3-phenyl-3-(4-p-tolyloxy-phenoxy)-propyl]-amino}-acetic acid
({3-[4-(4-Methoxy-phenoxy)-phenoxy]-3-phenyl-propyl}-methyl-amino)-acetic acid
({3-[4-(4-Chloro-phenoxy)-phenoxy]-3-phenyl-propyl}-methyl-amino)-acetic acid
(Methyl-{3-[4-(naphthalen-2-yloxy)-phenoxy]-3-phenyl-propyl}-amino)-acetic acid
({3-[4-(4-Isopropyl-phenoxy)-phenoxy]-3-phenyl-propyl}-methyl-amino)-acetic acid
({3-[4-(4-tert-Butyl-phenoxy)-phenoxy]-3-phenyl-propyl}-methyl-amino)-acetic acid
(Methyl-{3-phenyl-3-[4-(5,6,7,8-tetrahydro-naphthalen-2-yloxy)-phenoxy]-propyl}-amino)-acetic acid
({3-[4-(3,4-Dimethyl-phenoxy)-phenoxy]-3-phenyl-propyl}-methyl-amino)-acetic acid
({3-[4-(Indan-5-yloxy)-phenoxy]-3-phenyl-propyl}-methyl-amino)-acetic acid
({3-[4-(2,4-Difluoro-phenoxy)-phenoxy]-3-phenyl-propyl}-methyl-amino)-acetic acid
({3-(4-Fluoro-phenyl)-3-[4-(5,6,7,8-tetrahydro-naphthalen-1-yloxy)-phenoxy]-propyl}-methyl-amino)-acetic acid
{[3-[4-(2,4-Dimethyl-phenoxy)-phenoxy]-3-(4-fluoro-phenyl)-propyl]-methyl-amino}-acetic acid
({3-(4-Fluoro-phenyl)-3-[4-(2,4,6-trimethyl-phenoxy)-phenoxy]-propyl}-methyl-amino)-acetic acid
(Methyl-{3-phenyl-3-[4-(5,6,7,8-tetrahydro-naphthalen-1-yloxy)-phenoxy]-propyl}-amino)-acetic acid
({3-[4-(2,4-Dimethyl-phenoxy)-phenoxy]-3-phenyl-propyl}-methyl-amino)-acetic acid
{[3-[4-(4-Cyclohexyl-phenoxy)-phenoxy]-3-(4-fluoro-phenyl)-propyl]-methyl-amino}-acetic acid
{[3-[4-(4-Cyclopentyl-phenoxy)-phenoxy]-3-(4-fluoro-phenyl)-propyl]-methyl-amino}-acetic acid
({3-[4-(4-Cyclohexyl-phenoxy)-phenoxy]-3-phenyl-propyl}-methyl-amino)-acetic acid
({3-[4-(4-Cyclopentyl-phenoxy)-phenoxy]-3-phenyl-propyl}-methyl-amino)-acetic acid
{[3-[4-(2,3-Dihydro-benzo[1,4]dioxin-5-yloxy)-phenoxy]-3-(4-fluoro-phenyl)-propyl]-methyl-amino}-acetic acid
({3-[4-(2,3-Dihydro-benzo[1,4]dioxin-5-yloxy)-phenoxy]-3-phenyl-propyl}-methyl-amino)-acetic acid
{[3-[4-(2,3-Dihydro-benzofuran-7-yloxy)-phenoxy]-3-(4-fluoro-phenyl)-propyl]-methyl-amino}-acetic acid
({3-[4-(2,3-Dihydro-benzofuran-7-yloxy)-phenoxy]-3-phenyl-propyl}-methyl-amino)-acetic acid
{[3-[4-(Benzofuran-4-yloxy)-phenoxy]-3-(4-fluoro-phenyl)-propyl]-methyl-amino}-acetic acid
({3-[4-(2,3-Dihydro-benzofuran-4-yloxy)-phenoxy]-3-phenyl-propyl}-methyl-amino)-acetic acid
{[3-[4-(2,3-Dihydro-benzofuran-4-yloxy)-phenoxy]-3-(4-fluoro-phenyl)-propyl]-methyl-amino}-acetic acid
{[3-[4-(3,5-Bis-trifluoromethyl-phenoxy)-phenoxy]-3-(4-fluoro-phenyl)-propyl]-methyl-amino}-acetic acid
({3-(4-Fluoro-phenyl)-3-[4-(4-trifluoromethoxy-phenoxy)-phenoxy]-propyl}-methyl-amino)-acetic acid
(Methyl-{3-phenyl-3-[4-(4-trifluoromethoxy-phenoxy)-phenoxy]-propyl}-amino)-acetic acid
{[3-[4-(Benzo[1,3]dioxol-5-yloxy)-phenoxy]-3-(4-fluoro-phenyl)-propyl]-methyl-amino}-acetic acid
({3-[4-(Benzo[1,3]dioxol-5-yloxy)-phenoxy]-3-phenyl-propyl}-methyl-amino)-acetic acid
({3-[4-(3-Methoxy-phenoxy)-phenoxy]-3-phenyl-propyl}-methyl-amino)-acetic acid
({3-(4-Fluoro-phenyl)-3-[4-(3-methoxy-phenoxy)-phenoxy]-propyl}-methyl-amino)-acetic acid
(Methyl-{3-phenyl-3-[4-(3-trifluoromethoxy-phenoxy)-phenoxy]-propyl}-amino)-acetic acid
({3-(4-Fluoro-phenyl)-3-[4-(3-trifluoromethoxy-phenoxy)-phenoxy]-propyl}-methyl-amino)-acetic acid
({3-[4-(2-Methoxy-phenoxy)-phenoxy]-3-phenyl-propyl}-methyl-amino)-acetic acid
({3-(4-Fluoro-phenyl)-3-[4-(2-methoxy-phenoxy)-phenoxy]-propyl}-methyl-amino)-acetic acid
({3-[4-(3,4-Dimethoxy-phenoxy)-phenoxy]-3-phenyl-propyl}-methyl-amino)-acetic acid
{[3-[4-(3,4-Dimethoxy-phenoxy)-phenoxy]-3-(4-fluoro-phenyl)-propyl]-methyl-amino}-acetic acid
({3-[4-(2,3-Dihydro-benzo[1,4]dioxin-6-yloxy)-phenoxy]-3-phenyl-propyl}-methyl-amino)-acetic acid
{[3-[4-(2,3-Dihydro-benzo[1,4]dioxin-6-yloxy)-phenoxy]-3-(4-fluoro-phenyl)-propyl]-methyl-amino}-acetic acid
{Methyl-[3-(3-methyl-4-p-tolyloxy-phenoxy)-3-phenyl-propyl]-amino}-acetic acid ({3-(4-Fluoro-phenyl)-3-[4-(4-methoxy-phenoxy)-3-methyl-phenoxy]-propyl}-methyl-amino)-acetic acid
{[3-4-(Benzo[1,3]dioxol-5-yloxy)-phenoxy]-3-(4-chloro-phenyl)-propyl]-methyl-amino}-acetic acid
({3-(4-Fluoro-phenyl)-3-[4-(3-methoxy-phenoxy)-phenoxy]-propyl}-methyl-amino)-acetic acid
{[3-[4-(3-Methoxy-phenoxy)-phenoxy]-3-(4-methoxy-phenyl)-propyl]-methyl-amino}-acetic acid
({3-(4-Chloro-phenyl)-3-[4-(3-methoxy-phenoxy)-phenoxy]-propyl}-methyl-amino)-acetic acid
{[3-[4-(4-Methoxy-phenoxy)-phenoxy]-3-(4-methoxy-phenyl)-propyl]-methyl-amino}-acetic acid
({3-(4-Chloro-phenyl)-3-[4-(4-methoxy-phenoxy)-phenoxy]-propyl}-methyl-amino)-acetic acid
{[3-[2-Chloro-4-(4-methoxy-phenoxy)-phenoxy]-3-(4-fluoro-phenyl)-propyl]-methyl-amino}-acetic acid
{[3-(4-Fluoro-phenyl)-3-(3-methyl-4-phenoxy-phenoxy)-propyl]-methyl-amino}-acetic acid
{[3-[4-(Benzo[1,3]dioxol-5-yloxy)-phenoxy]-3-(4-methoxy-phenyl)-propyl]-methyl-amino}-acetic acid
{[3-[2-Chloro-4-(4-methoxy-phenoxy)-phenoxy]-3-(4-methoxy-phenyl)-propyl]-methyl-amino}-acetic acid
{[3-[3-Methoxy-4-(4-methoxy-phenoxy)-phenoxy]-3-(4-methoxy-phenyl)-propyl]-methyl-amino}-acetic acid
({3-(4-Fluoro-phenyl)-3-[3-methoxy-4-(4-methoxy-phenoxy)-phenoxy]-propyl}-methyl-amino)-acetic acid
({3-(4-Fluoro-phenyl)-3-[3-methoxy-4-(3-methoxy-phenoxy)-phenoxy]-propyl}-methyl-amino)-acetic acid
({3-[3-Methoxy-4-(3-methoxy-phenoxy)-phenoxy]-3-phenyl-propyl}-methyl-amino)-acetic acid
({3-[3-Methoxy-4-(4-methoxy-phenoxy)-phenoxy]-3-phenyl-propyl}-methyl-amino)-acetic acid
({3-[4-(3-Methoxy-phenoxy)-2-methyl-phenoxy]-3-phenyl-propyl}-methyl-amino)-acetic acid
{[3-[3-Methoxy-4-(3-methoxy-phenoxy)-phenoxy]-3-(4-methoxy-phenyl)-propyl]-methyl-amino}-acetic acid
{[3-(3-Methoxy-4-phenoxy-phenoxy)-3-phenyl-propyl]-methyl-amino}-acetic acid
{[3-(4-Fluoro-phenyl)-3-(3-methoxy-4-phenoxy-phenoxy)-propyl]-methyl-amino}-acetic acid
{[3-(4-Fluoro-phenyl)-3-(2-methyl-4-phenoxy-phenoxy)-propyl]-methyl-amino}-acetic acid
{Methyl-[3-(2-methyl-4-phenoxy-phenoxy)-3-phenyl-propyl]-amino}-acetic acid
({3-[4-(4-Methoxy-phenoxy)-2-methyl-phenoxy]-3-phenyl-propyl}-methyl-amino)-acetic acid
({3-[4-(4-Chloro-phenoxy)-2-methyl-phenoxy]-3-phenyl-propyl}-methyl-amino)-acetic acid
{Methyl-[3-(2-methyl-4-p-tolyloxy-phenoxy)-3-phenyl-propyl]-amino}-acetic acid
{[3-(2-Chloro-4-phenoxy-phenoxy)-3-(4-fluoro-phenyl)-propyl]-methyl-amino}-acetic acid
{[3-(2-Chloro-4-p-tolyloxy-phenoxy)-3-(4-fluoro-phenyl)-propyl]-methyl-amino}-acetic acid
{[3-[2-Chloro-4-(4-chloro-phenoxy)-phenoxy]-3-(4-fluoro-phenyl)-propyl]-methyl-amino}-acetic acid
{Methyl-[3-(3-phenoxy-phenoxy)-3-phenyl-propyl]-amino}-acetic acid
{[3-(4-Fluoro-phenyl)-3-(3-phenoxy-phenoxy)-propyl]-methyl-amino}-acetic acid
{[3-(4-Fluoro-phenyl)-3-(3-p-tolyloxy-phenoxy)-propyl]-methyl-amino}-acetic acid
({3-(4-Fluoro-phenyl)-3-[3-(4-methoxy-phenoxy)-phenoxy]-propyl}-methyl-amino)-acetic acid
({3-[3-(4-Chloro-phenoxy)-phenoxy]-3-phenyl-propyl}-methyl-amino)-acetic acid
{[3-[3-(4-Chloro-phenoxy)-phenoxy]-3-(4-fluoro-phenyl)-propyl]-methyl-amino}-acetic acid
({3-(4-Fluoro-phenyl)-3-[3-(2-methoxy-phenoxy)-phenoxy]-propyl}-methyl-amino)-acetic acid
{[3-(4-Fluoro-phenyl)-3-(4-methyl-3-phenoxy-phenoxy)-propyl]-methyl-amino}-acetic acid
({3-(4-Fluoro-phenyl)-3-[3-(3-methoxy-phenoxy)-4-methyl-phenoxy]-propyl}-methyl-amino)-acetic acid
({3-(4-Fluoro-phenyl)-3-[3-(4-methoxy-phenoxy)-4-methyl-phenoxy]-propyl}-methyl-amino)-acetic acid
{[3-[3-(Benzo[1,3]dioxol-5-yloxy)-4-methyl-phenoxy]-3-(4-fluoro-phenyl)-propyl]-methyl-amino}-acetic acid
(Methyl-{3-phenyl-3-[4-(pyridin-4-yloxy)-phenoxy]-propyl}-amino)-acetic acid
({3-(4-Fluoro-phenyl)-3-[4-(pyridin-4-yloxy)-phenoxy]-propyl}-methyl-amino)-acetic acid
(Methyl-{3-phenyl-3-[4-(pyridin-3-yloxy)-phenoxy]-propyl}-amino)-acetic acid
({3-(4-Fluoro-phenyl)-3-[4-(pyridin-3-yloxy)-phenoxy]-propyl}-methyl-amino)-acetic acid
(Methyl-{3-phenyl-3-[4-(pyridin-2-yloxy)-phenoxy]-propyl}-amino)-acetic acid
({3-(4-Fluoro-phenyl)-3-[4-(pyridin-2-yloxy)-phenoxy]-propyl}-methyl-amino)-acetic acid This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, and senile dementia of the Alzheimer's type) and memory disorders in a mammal, including a human, comprising administering to a mammal in need of such treatment an amount of a compound of the formula I, or a pharmaceutically acceptable salt thereof, that is effective in treating such condition or disorder.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in an amount that is effective for treating such disorder or condition.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising administering to a mammal in need of such treatment a glycine transport-inhibiting amount of a compound of the formula I, or a pharmaceutically acceptable salt thereof.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in a glycine transport-inhibiting amount.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, isobutyl, sec-butyl, tert-butyl, pentyl, hexyl, heptyl, 3-ethylbutyl, cyclopropyl, cyclobutyl, cyclopentyl, cyclohexyl, cycloheptyl, norbornyl, and the like.

The term "halo", as used herein, means chloro, fluoro, iodo or bromo.

The term "alkoxy", as used herein, means "alkyl-O—", wherein "alkyl" is defined as above.

The term "treating", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritium and $^{14}C$ isotopes are particularly preferred for their ease of preparation and detectability. Further, substitution with heavier isotopes such as deuterium can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Scheme and/or in the Examples and Preparations below, by substituting a readily available isotopically labelled reagent for a non-isotopically labelled reagent.

DETAILED DESCRIPTION OF THE INVENTION

The compounds of the formula (I) of this invention may be prepared as described in the following reaction schemes.

Unless otherwise indicated, in the reaction schemes and discussion that follow, X and Y are defined as above.

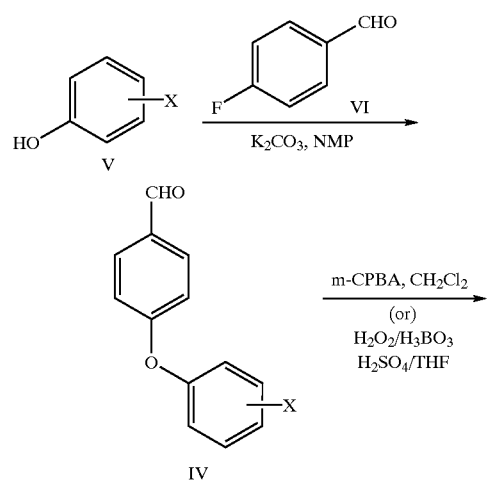

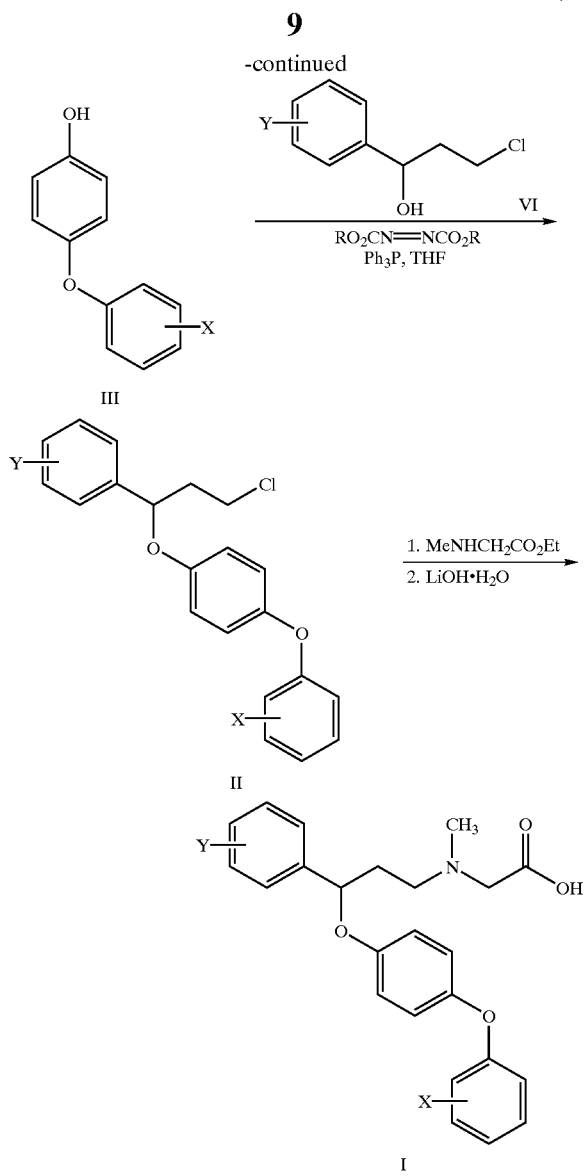

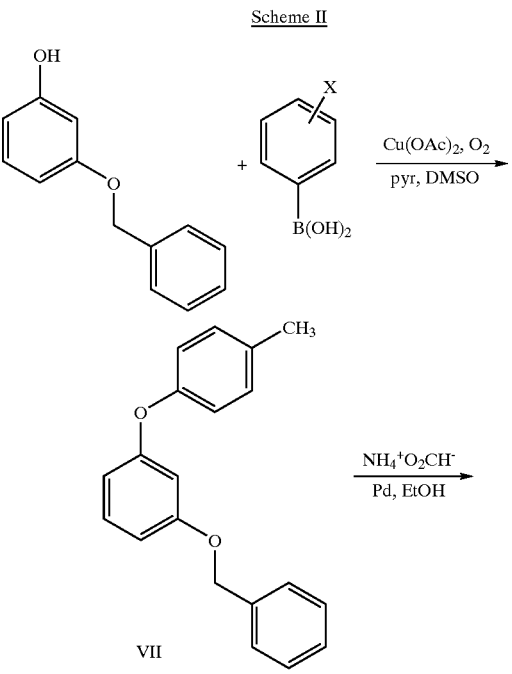

The phenolic alcohol compound of formula III is then treated with a haloalkyl-substituted benzylic alcohol of formula VI under conditions suited to form a haloalkylphenoxy aryl compound of formula II. This reaction is preferably carried out using a dialkyl azodicarboxylate in the presence of a trialkyl or triaryl phosphine. More preferably, the dialkyl azodicarboxylate is a diethyl azodicarboxylate, diisopropyl azodicarboxylate, or diisobutyl azodicarboxylate, and the phosphine is tri-n-butylphospine, triphenylphospine, or tri-p-tolylphospine. The reaction is typically performed in a dipolar ether such as THF, at a temperature from about 50° C. to about 120° C., preferably at about the reflux temperature of THF.

The compound of formula II is treated with an aminoacetic ester such as N-methyl glycine ethyl ester (sarcosine ethyl ester) in the presence of an organic base such as diisopropylethylamine or diethylamine. This reaction is typically conducted in a reaction-inert solvent such as N-methylpyrrolidinone or dimethyl formamide, at a temperature from about room temperature to about 150° C., preferably at about 90° C. Then, the resulting ester is hydrolyzed using an alkali metal carbonate or bicarbonate or an alkali metal hydroxide, preferably an alkali metal hydroxide, such as lithium hydroxide, in water, a mixture of water, an alcohol containing one to four carbons and/or an ethereal solvent such as tetrahydrofuran to form the corresponding carboxylic acid of formula I. The hydrolysis reaction can be carried out in situ or after isolating the ester from the alkylation reaction. In either case, the hydrolysis is carried out using the same or similar solvent as that used in the alkylation reaction and is carried out under the same or similar conditions.

Scheme II illustrates methods of preparing compounds of the formula I wherein ring A is in the 3- (or meta) position. Methods analogous to these can be used to prepare compounds of the formula I wherein ring A is other than phenyl. Such methods will be understood by those of skill in the art.

Scheme I illustrates methods of preparing compounds of the formula I wherein ring A is phenyl. Methods analogous to these can be used to prepare compounds of the formula I wherein ring A is other than phenyl. Such methods will be understood by those of skill in the art.

Referring to Scheme I, a compound of formula V is reacted with 4-fluorobenzaldehyde (VI) in the presence of an alkali metal or alkaline earth metal carbonate or bicarbonate to form the corresponding ether of formula IV. This reaction is typically conducted in a reaction-inert solvent such as dimethyl formamide (DMF), methyl pyrrolidone or dimethylacetamide, at a temperature from about 100° C. to about 170° C., preferably at about 150° C. The resulting compound of formula IV is then oxidized to the corresponding phenolic alcohol compound of formula III using a peracid, such as peracetic, trifluoroacetic, perbenzoic or m-chloroperbenzoic acid, in an inert organic solvent, such as dichloromethane. As an alternative, and especially when the X-bearing phenyl ring is a pyridyl ring, this oxidation may be carried out using hydrogen peroxide, preferably 30% strength, and boric acid, with a small amount of sulfuric acid, in an inert solvent such as tetrahydrofuran or dioxane, at a temperature from room temperature to the reflux temperature of the solvent, for 1 to 24 hours.

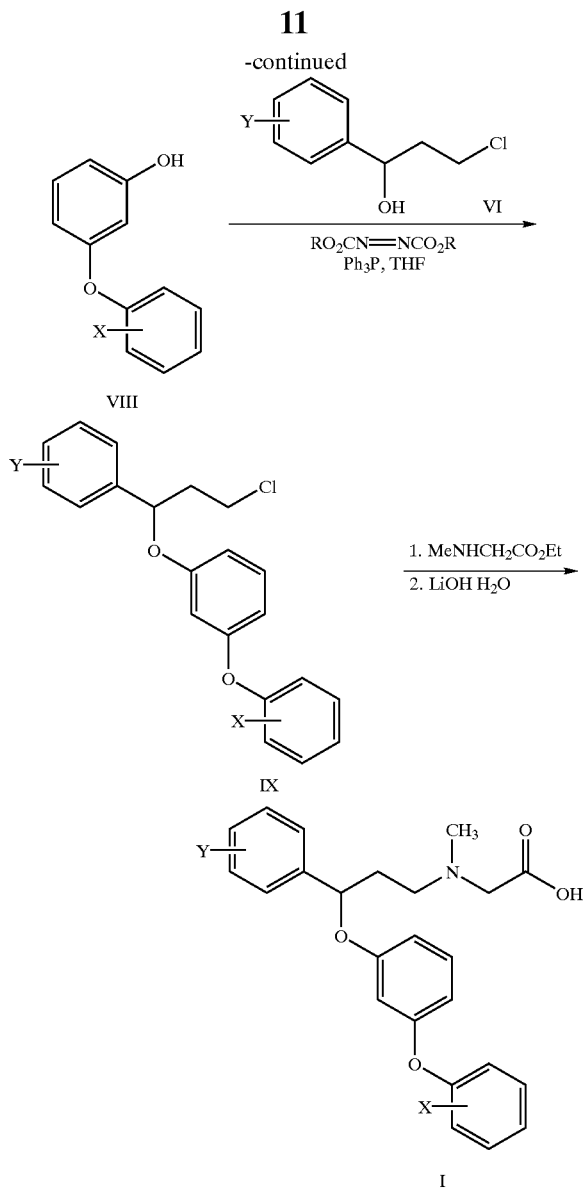

Referring to Scheme II, 3-benzyloxyphenol is reacted with an aryl boronic acid using cupric acetate, cupric trifluoroacetate, or a related copper salt, a base such as pyridine, triethylamine, or an organic amine base, and dimethylsulfoxide or methylene chloride as solvent under an oxygen atmosphere at room temperature to 100° C. for 12 to 100 hours to afford intermediate VII. Compound VII is then reacted to intermediate VIII by treating it with ammonium formate and palladium in ethanol or a higher alcohol. The reaction may also be carried out using palladium under a hydrogen atmosphere, or using boron tribromide in methylene chloride at −78° C. to room temperature for 1 to 24 hours. Intermediate VIII is then processed to compound IX as detailed above in Scheme 1 for compound II. Compound IX is then reacted as detailed in Scheme 1 to produce the compound of formula I.

The compounds of formula I and the intermediates shown in the above reaction schemes can be isolated and purified by conventional procedures, such as recrystallization or chromatographic separation.

In so far as the compounds of formula (I) of this invention can contain basic substituents, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1,1'-methylene-bis-(2-hydroxy-3-naphthoate))salts.

All compounds of the invention have an acidic group and are capable of forming base salts with various pharmaceutically acceptable cations. Examples of such salts include the alkali metal or alkaline-earth metal salts and, particularly, the sodium and potassium salts. These salts are all prepared by conventional techniques.

The chemical bases which are used as reagents to prepare the pharmaceutically acceptable base salts of this invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the aforementioned acidic compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of the present invention exhibit significant glycine transport inhibiting activity and therefore are of value in the treatment of a wide variety of clinical conditions that are characterized by the deficit of glutamateric neurotransmission in mammalian subjects, especially humans. Such conditions include the positive and negative symptoms of schizophrenia and other psychoses, and cognitive deficits.

The compounds of the formula (I) of this invention can be administered via either the oral, parenteral (such as subcutaneous, intraveneous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of the present invention were assayed for their activity in inhibiting glycine reuptake in synaptosomes by first preparing synaptosomes and then measuring neurotransmitter reuptake activity as follows:

Male Sprague Dawley rats were decapitated and the brains removed. The whole brains were dissected out and placed in ice cold sucrose buffer; 1 gram in 20 mis (320 mM sucrose containing 1 mg/ml glucose, 0.1 mM EDTA and brought up to pH 7.4 with Tris base). The tissue was homogenized in a glass homogenizing tube with a teflon pestle at 350 RPMS using a Potters homogenizer. The homogenate was centrifuged at 1000×g for 10 min at 4° C. The resulting supernatant was recentrifuged at 17,000×g for 20 min at 4° C. The final pellet was resuspended in an appropriate volume of sucrose buffer containing 5 mM alanine, to yield less than 10% uptake.

The uptake assays were conducted in 96 well matrix plates. Each well contained 25 µL of solvent, inhibitor or 10 mM glycine for nonspecific uptake, 200 µL of [$^3$H]-glycine (40 nM final), made up in modified Krebs containing 5 mM alanine and glucose (1 mg/ml) and 25 µL of synaptosomes. The plates were then incubated at room temperature for the 15 min. The incubation was terminated by filtration through GF/B filters, using a 96 well Brandel Cell Harvester. The filters were washed with modified Krebs buffer and either counted in a liquid scintillation counter or in a LKB Beta Plate counter. Compounds of the invention analyzed by this assay have been found to have significant activity in inhibiting glycine reuptake in synaptosomes, having IC$_{50}$ values more potent than 10 µM.

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a Varian NMR spectrometer (Unity, 400 MHz for $^1$H, 100 MHz for $^{13}$C) unless otherwise indicated and peak positions are expressed in parts per million (ppm) downfield from tetramethylsilane (δ). The peak shapes are denoted as follows: s, singlet; d, doublet; t, triplet; m, multiplet; br, broad.

EXAMPLE 1

(Methyl-{3-phenyl-3-[4-(3trifluoromethylphenoxy) phenoxy]propyl}amino)acetic Acid A. [4-(3-Trifluoromethyl)phenoxy]benzaldehyde As described in *Synthesis*, 63, (1991): To a 125 ml round-bottomed flask equipped with condenser and nitrogen gas inlet were added 1.07 ml (10 mmol) 4-fluorobenzaldehye, 1.22 ml (10 mmol) 3-trifluoromethylphenol, 1.66 g (12 mmol) potassium carbonate, and 10 ml dry N-methylpyrrolidin-2-one. The reaction was heated at 150° C. for 14 hours (h), and the black mixture cooled to room temperature, poured into water, and extracted into ethyl acetate. The organic layer was washed with several portions of water, brine, then dried over sodium sulfate and evaporated. The residue was filtered through silica gel with hexane/ethyl acetate to afford a yellow oil, 2.46 g (92.5%).

$^1$H-NMR (δ, CDCl$_3$): 7.05 (m, 2H), 7.23 (m, 1H), 7.305 (m, 1H), 7.4–7.6 (m, 2H), 7.84 (m, 2H), 9.92 (s, 1H).

$^{13}$C-NMR (δ, CDCl$_3$): 117.24, 118.36, 121.54, 121.62, 123.52, 130.97, 132.28, 155.89, 162.26, 190.85 (signals for the CF$_3$ and adjacent carbon not visible in this scan).

B. [4-(3-Trifluoromethyl)phenoxy]phenol

As described in *Synthesis*, page 63, 1991: To a 125 mL round-bottomed flask equipped with condenser and a nitrogen inlet were added 2.46 g (9.25 mmol) [4-(3-trifluoromethyl)phenoxy]benzaldehyde, 2.39 g (11.1 mmol) m-chloroperbenzoic acid (80%), and 25 ml dry methylene chloride. The reaction was stirred at room temperature for 8 hr, filtered, and the filtrate washed with aqueous sodium bisulfite solution, aqueous sodium bicarbonate solution, dried over sodium sulfate, and evaporated. The residue was taken up in 50 ml methanol, treated with 3 drops concentrated hydrochloric acid, and stirred at room temperature for 14 h. The residue after evaporation was filtered through silica gel using ethyl acetate and hexane to afford 2.48 g (100%) of an oil.

$^1$H-NMR ($\delta$, CDCl$_3$): 6.84 (m, 2H), 6.90 (m, 2H), 7.05 (m, 1H), 7.13 (m, 1H), 7.24 (m, 1H), 7.35 (m, 1H).

$^{13}$C-NMR ($\delta$, CDCl$_3$): 114.17, 116.80, 119.03, 120.56, 121.61, 130.33, 148.96, 153.12, 159.23 (signals for the CF$_3$ and adjacent carbon not visible in this scan).

C. 3-Phenyl-3-[4-(3-trifluoromethylphenoxy)phenoxy]-1-chloropropane

To a 125 mL round-bottomed flask equipped with a nitrogen inlet were added 0.50 g (2.93 mmol) 3-chloro-1-phenylpropanol, 745 mg (2.93 mmol) [4-(3-trifluoromethyl)phenoxy]phenol, 0.64 ml (3.22 mmol) diisopropylazodicarboxylate, 0.85 g (3.22 mmol) triphenylphosphine, and 15 ml dry tetrahydrofuran. The reaction was refluxed for 14 h, cooled, and evaporated. The residue was chromatographed on silica gel using ethyl acetate in hexane as eluant to afford 486 mg (41%) of an oil.

$^1$H-NMR ($\delta$, CDCl$_3$): 2.21 and 2.47 (multiplets, 2H), 3.61 and 3.82 (multiplets, 2H), 5.33 (m, 1H), 6.85 (m, 4H), 7.04 (m, 1H), 7.26 (m, 1H), 7.2–7.4 (m, 7H).

$^{13}$C-NMR ($\delta$, CDCl$_3$): 41.53, 41.58, 77.70, 117.55, 119.19, 119.22, 119.26, 120.78, 121.12, 126.17, 128.24, 129.05, 130.35, 140.89, 149.63, 158.90 (signals for the CF$_3$ and adjacent carbon not visible in this scan).

D. (Methyl-{3-phenyl-3-[4-(3-trifluoromethylphenoxy)phenoxy]propyl}amino) acetic Acid Ethyl Ester To a 125 mL round-bottomed flask equipped with condenser and nitrogen inlet were added 486 mg (1.20 mmol) 3-phenyl-3-[4-(3-trifluoromethyl-phenoxy)-phenoxy]-1-chloropropane, 184 mg (1.20 mmol) sarcosine ethyl ester hydrochloride, 0.416 mL (2.40 mmol) diisopropylethylamine, and 6 mL dry N-methylpyrrolidinone. The reaction was heated at 90–95° C. for 60 h, cooled, and poured into water. After extracting with ethyl acetate, the organic layer was washed with water (3 times) and brine, dried over sodium sulfate, and evaporated. The residue was chromatographed on silica gel using methylene chloride/methanol as eluant to afford 250 mg (43%) of an oil.

$^1$H-NMR ($\delta$, CDCl$_3$): 1.22 (t, J=7, 3H), 1.99 and 2.18 (multiplets, 2H), 2.38 (s, 3H), 2.68 (m, 2H), 3.24 (s, 2H), 4.12 (q, J=7, 2H), 5.18 (m, 1H), 6.83 (s, 4H), 7.02 (m, 1H), 7.10 (m, 1H), 7.2–7.4 (m, 7H).

$^{13}$C-NMR ($\delta$, CDCl$_3$): 14.46, 36.88, 42.51, 53.46, 58.82, 60.69, 78.99, 114.44, 117.48, 119.11, 120.69, 121.09, 126.20, 127.87, 128.86, 130.30, 141.91, 149.28, 155.25, 155.27, 158.99 (signals for the CF$_3$ and adjacent carbon not visible in this scan).

MS (%): 488 (parent+1, 100).

E. (Methyl-{3-phenyl-3-[4-(3-trifluoromethylphenoxy)phenoxy]propyl}amino) acetic Acid To a 125 mL round-bottomed flask equipped with condenser and nitrogen inlet were added 250 mg (0.514 mmol) {[3-(4-(3-trifluoromethyl)phenoxy)phenoxy)-3-phenylpropyl]methylamino}-acetic acid ethyl ester, 6 ml tetrahydrofuran, a solution of 100 mg lithium hydroxide hydrate in 10 ml water, and enough methanol to afford a solution. The reaction was stirred at room temperature for 1 h, evaporated, and taken up in water to pH 1 with 6 N hydrochloric acid. The aqueous layer was extracted with several portions of methylene chloride, and the organic layer washed with brine, dried over sodium sulfate, and evaporated to a foam, 225 mg (38%).

$^{13}$C-NMR ($\delta$, CDCl$_3$): 33.32, 41.76, 54.53, 56.62, 78.02, 114.45, 117.61, 119.28, 120.77, 121.11, 123.92 (q, J=269, CF$_3$), 126.14, 128.46, 129.16, 130.40, 132.17 (q, J=29), 140.10, 149.76, 154.26, 158.71, 167.44.

MS (%): 460 (parent+1, 100).

Anal. Calc'd. for C$_{25}$H$_{24}$NO$_4$F$_3$.HCl: C, 60.55; H, 5.08; N, 2.82. Found: C, 60.65; H, 5.64; N, 2.60.

EXAMPLE 2

{Methyl-[3-phenyl-3-(4-p-tolyloxyphenoxy)propyl]amino}acetic Acid

Prepared as in Example 1, in 9.5% yield, as a foam.

$^{13}$C-NMR ($\delta$, CDCl$_3$): 33.36, 41.73, 54.45, 56.67, 78.02, 117.32, 117.98, 118.29, 120.10, 126.17, 128.36, 129.01, 129.11, 130.33, 132.45, 132.64, 140.34, 151.52, 153.38, 155.75, 167.66.

MS (%): 406 (parent+1, 100).

Anal. Calc'd. for C$_{25}$H$_{27}$NO$_4$HCl.1/4H$_2$O: C, 67.26; H, 6.43; N, 3.14. Found: C, 67.04; H, 7.00; N, 2.96.

EXAMPLE 3

({3-[4-(4-Methoxyphenoxy)phenoxy]-3-phenylproyl}methylamino)-acetic Acid

Prepared as in Example 1, in 43% yield, as a foam.

$^{13}$C-NMR ($\delta$, CDCl$_3$): 33.38, 41.54, 41.93, 54.55, 56.39, 77.96, 114.96, 117.33, 119.30, 120.02, 126.18, 128.35, 129.10, 140.32, 151.19, 152.34, 153.05, 155.65, 167.18.

MS (%): 422 (parent+1, 100).

Anal. Calc'd. for C$_{25}$H$_{27}$NO$_5$.HCl.H$_2$O: C, 63.09; H, 6.35; N, 2.94. Found: C, 62.84; H, 6.43; N, 3.34.

EXAMPLE 4

({3-[4-(4-Chlorophenoxy)phenoxy]-3-phenylpropyl}methylamino)acetic Acid

Prepared as in Example 1, in 37% yield, as a foam.

$^{13}$C-NMR ($\delta$, CDCl$_3$): 33.35, 41.86, 53.69, 54.46, 56.60, 78.00, 117.45, 119.20, 120.69, 126.13, 127.73, 128.45, 129.15, 129.76, 140.17, 150.51, 153.89, 156.88, 167.56.

MS (%): 426 (parent+1, 100).

Anal. Calc'd. for C$_{24}$H$_{24}$NO$_4$Cl.HCl.H$_2$O: C, 60.01; H, 5.67; N, 2.92. Found: C, 60.16; H, 5.36; N, 2.69.

EXAMPLE 5

(Methyl-{3-[4-(naphthalen-2-yloxy)phenoxy]-3-phenylpropyl}amino)acetic Acid

Prepared as in Example 1, in 23% yield, as a foam.

$^{13}$C-NMR ($\delta$, CDCl$_3$): 33.39, 41.60, 42.01, 54.66, 56.47, 78.03, 112.87, 117.50, 119.59, 120.86, 124.68, 126.20, 126.71, 127.23, 127.88, 128.43, 129.16, 129.99, 130.02, 134.45, 140.23, 150.80, 153.82, 156.09, 167.06.

MS (%): 442 (parent+1, 100).

Anal. Calc'd. for $C_{28}H_{27}NO_4 \cdot HCl \cdot 3/2H_2O$: C, 66.59; H, 6.19; N, 2.77. Found: C, 66.37; H, 6.01; N, 2.82.

EXAMPLE 6

({3-[4-(4-Isopropylphenoxy)phenoxy]-3-phenylpropyl}methylamino)acetic Acid

Prepared as in Example 1, in 24% yield, as a foam.

$^{13}$C-NMR ($\delta$, CDCl$_3$): 24.35, 33.04, 33.59, 41.63, 42.05, 54.70, 55.75, 56.36, 78.02, 117.33, 118.13, 120.25, 126.18, 127.66, 128.37, 129.12, 140.26, 143.51, 151.45, 153.38, 155.95, 166.82.

MS (%): 434 (parent+1, 100).

Anal. Calc'd. for $C_{27}H_{31}NO_4 \cdot HCl \cdot 3/4H_2O$: C, 67.07; H, 6.98; N, 2.90. Found: C, 67.32; H, 7.22; N, 2.73.

EXAMPLE 7

({3-[4-(4-t-Butylphenoxy)phenoxy]-3-phenylpropyl}methylamino)acetic Acid

Prepared as in Example 1, in 39% yield, as a foam.

$^{13}$C-NMR ($\delta$, CDCl$_3$): 31.73, 33.34, 34.46, 41.81, 54.57, 56.56, 78.06, 117.44, 117.74, 120.37, 125.77, 126.27, 126.67, 128.38, 129.15, 140.40, 145.76, 151.35, 153.49, 155.73, 167.50.

MS (%): 448 (parent+1, 100).

Anal. Calc'd. for $C_{28}H_{33}NO_4 \cdot HCl \cdot 2H_2O$: C, 64.67; H, 7.36; N, 2.69. Found: C, 64.89; H, 7.18; N, 2.70.

EXAMPLE 8

(Methyl-{3-phenyl-3-[4-(5,6,7,8-tetrahydronaphthalen-2-yloxy)phenoxy]propyl}amino)acetic Acid Prepared as in Example 1, in 29% yield, as a foam.

$^{13}$C-NMR ($\delta$, CDCl$_3$): 23.21, 23.48, 28.90, 29.71, 33.04, 33.39, 41.68, 42.10, 53.71, 54.65, 55.81, 56.44, 78.03, 115.85, 117.33, 118.56, 120.12, 126.22, 128.35, 129.11, 130.31, 131.80, 138.75, 140.29, 151.53, 153.27, 155.56, 167.10.

MS (%): 446 (parent+1, 100).

Anal. Calc'd. for $C_{28}H_{31}NO_4 \cdot HCl \cdot 3/2H_2O$: C, 66.07; H, 6.93; N, 2.75. Found: C, 66.36; H, 7.10; N, 2.80.

EXAMPLE 9

(Methyl-{3-phenyl-3-[4-(4-trifluoromethylphenoxy)phenoxy]proryl}amino)acetic Acid Prepared as in Example 1, in 41.5% yield, as a foam.

$^{13}$C-NMR ($\delta$, CDCl$_3$): 33.39, 41.67, 53.71, 54.32, 56.62, 78.10, 117.18, 117.54, 121.49, 123.06, 124.47 (q, J=33), 124.59 (q, J=270, CF$_3$), 127.17, 127.21, 128.46, 129.15, 140.13, 149.36, 154.44, 161.25, 167.86.

MS (%): 460 (parent+1, 100).

Anal. Calc'd. for $C_{25}H_{24}NO_4F_3 \cdot HCl \cdot H_2O$: C, 58.43; H, 5.30; N, 2.73. Found: C, 58.80; H, 5.22; N, 2.85.

EXAMPLE 10

({3-(4-Fluoro-phenyl)-3-[4-(5,6,7,8-tetrahydro-naphthalen-1-yloxy)-phenoxy]-propyl}-methyl-amino)-acetic Acid Prepared as in Example 1, in 93% yield, as a solid, mp 60–61° C.

$^{13}$C-NMR ($\delta$, CDCl$_3$): 22.84, 22.99, 23.47, 25.82, 29.73, 33.89, 41.58, 53.74, 58.74, 68.16, 77.65, 115.28, 115.99 (d, J=22), 117.19, 119.25, 124.34, 126.05, 127.85 (d, J=8), 128.73, 136.45, 136.48, 139.52, 151.86, 152.94, 155.27, 162.50 (d, J=246), 168.80.

MS (%): 464 (parent+1, 100).

HRMS Calc'd. for $C_{28}H_{31}NO_4F$: 464.2238. Found: 464.2218.

EXAMPLE 11

{[3-[4-(2,4-Dimethyl-phenoxy)-phenoxy]-3-(4-fluoro-phenyl)-propyl]-methyl-amino}-acetic Acid Prepared as in Example 1, in 98% yield, as a foam.

$^{13}$C-NMR ($\delta$, CDCl$_3$): 16.29, 20.87, 33.51, 41.57, 53.99, 58.39, 77.6, 116.00 (d, J=22), 117.24, 118.43, 119.16, 127.69, 127.91 (d, J=7), 129.41, 132.20, 133.31, 133.33, 136.25, 136.28, 152.51, 152.54, 152.85, 162.50 (d, J=246), 168.65.

MS (%): 438 (parent+1, 100).

HRMS Calc'd. for $C_{26}H_{29}NO_4F$: 438.2081. Found: 438.2111.

EXAMPLE 12

({3-(4-Fluoro-phenyl)-3-[4-(2,4,6-trimethyl-phenoxy)-phenoxy]-propyl}-methyl-amino)-acetic Acid Prepared as in Example 1, in 100% yield, as a foam.

$^{13}$C-NMR ($\delta$, CDCl$_3$): 14.38, 16.43, 20.93, 21.07, 21.24, 33.38, 41.72, 54.36, 57.76, 60.63, 115.35, 115.97 (d, J=21), 117.25, 127.89 (d, J=8), 129.73, 131.12, 134.51, 136.23, 136.26, 149.22, 151.59, 152.83, 162.50 (d, J=246), 168.53, 171.46, 175.44.

MS (%): 452 (parent+1, 100).

HRMS Calc'd. for $C_{29}H_{30}NO_4F$: 452.2238. Found: 452.2255.

EXAMPLE 13

(Methyl-{3-phenyl-3-[4-(5,6,7,8-tetrahydro-naphthalen-1-yloxy)-phenoxy]-propyl}-amino)-acetic Acid Prepared as in Example 1, in 100% yield, as a foam.

$^{13}$C-NMR ($\delta$, CDCl$_3$): 22.87, 23.00, 23.49, 29.75, 33.36, 41.69, 54.36, 56.96, 60.66, 78.12, 115.16, 117.34, 119.36, 124.26, 126.07, 126.21, 128.30, 128.60, 129.08, 139.45, 140.45, 151.71, 153.08, 155.37, 168.25.

MS (%): 446 (parent+1, 100).

Anal. Calc'd. for $C_{28}H_{31}NO_4 \cdot HCl \cdot H_2O$: C, 67.26; H, 6.85; N, 2.80. Found: C, 67.45; H, 6.89; N, 2.69.

EXAMPLE 14

({3-[4-(2,4-Dimethyl-phenoxy)-phenoxy]-3-phenyl-proyyl}-methyl-amino)-acetic Acid Prepared as in Example 1, in 100% yield, as a solid, mp 53–55° C.

$^{13}$C-NMR ($\delta$, CDCl$_3$): 16.32, 20.87, 33.77, 41.49, 53.71, 58.62, 60.59, 78.26, 117.13, 118.46, 119.11, 126.07, 127.67, 128.22, 129.04, 129.37, 132.17, 133.15, 140.73, 152.30, 152.92, 153.00, 168.82.

MS (%): 420 (parent+1, 100).

Anal. Calc'd. for $C_{26}H_{29}NO_4 \cdot HCl \cdot H_2O$: C, 65.88; H, 6.80; N, 2.96. Found: C, 66.08; H, 6.96; N, 2.93.

EXAMPLE 15

{[3-[4-(4-Cyclohexyl-phenoxy)-phenoxy]-3-(4-fluoro-phenyl)-propyl]-methyl-amino}-acetic Acid Prepared as in Example 1, in 85% yield, as a foam.

$^{13}$C-NMR ($\delta$, CDCl$_3$): 21.70, 26.33, 27.10, 33.34, 34.85, 41.87, 44.02, 54.31, 59.00, 77.66, 116.06 (d, J=21), 117.27, 118.13, 119.54, 120.27, 127.92 (d, J=8), 128.06, 136.27, 136.30, 142.90, 151.61, 153.25, 155.94, 155.97, 162.58 (d, J=246), 169.80, 176.69.

MS (%): 492 (parent+1, 100).

EXAMPLE 16

{[3-[4-(4-Cyclopentyl-phenoxy)-phenoxy]-3-(4-fluoro-phenyl)-propyl]-methyl-amino}-acetic Acid Prepared as in Example 1, in 88% yield, as a foam.

$^{13}$C-NMR ($\delta$, CDCl$_3$): 25.62, 34.90, 41.62, 45.45, 53.75, 58.93, 60.60, 116.01 (d, J=21), 117.25, 118.15, 120.22, 127.89 (d, J=9), 128.36, 136.49, 141.17, 151.58, 153.34, 155.92, 162.52, (d, J=245), 168.96, 171.36.

MS (%): 478 (parent+1, 100).

EXAMPLE 17

({3-[4-(4-Cyclohexyl-phenoxy)-phenoxy]-3-phenyl-propyl}-methyl-amino)-acetic Acid Prepared as in Example 1, in 98.5% yield, as a foam.

$^{13}$C-NMR ($\delta$, CDCl$_3$): 26.32, 27.09, 29.65, 33.66, 34.82, 41.71, 43.99, 53.99, 59.10, 78.18, 117.14, 118.05, 120.29, 126.04, 128.00, 128.30, 129.09, 140.53, 142.77, 151.37, 153.50, 156.02, 168.57.

MS (%): 474 (parent+1, 100).

HRMS Calc'd. for $C_{30}H_{36}NO_4$: 474.2645. Found: 474.2642.

EXAMPLE 18

({3-[4-(4-Cyclopentyl-phenoxy)-phenoxy]-3-phenyl-propyl}-methyl-amino)-acetic Acid Prepared as in Example 1, in 93% yield, as a yellowish solid.

$^{13}$C-NMR ($\delta$, CDCl$_3$): 14.40, 25.60, 33.71, 34.88, 41.69, 45.44, 53.89, 60.59, 78.22, 117.14, 118.08, 120.22, 126.04, 128.30, 129.07, 140.60, 141.05, 151.38, 153.53, 155.99, 168.66.

MS (%): 460 (parent+1, 100).

HRMS Calc'd. for $C_{29}H_{34}NO_4$: 460.2488. Found: 460.2513.

EXAMPLE 19

{[3-[4-(2,3-Dihydro-benzo[1,4]dioxin-5-yloxy)-phenoxy]-3-(4-fluoro-phenyl)-propyl]-methyl-amino}-acetic Acid Prepared as in Example 1, in 91% yield, as a foam.

$^{13}$C-NMR ($\delta$, CDCl$_3$): 14.38, 21.39, 33.41, 41.60, 54.01, 58.53, 60.60, 64.41, 64.60, 77.63, 111.94, 112.64, 115.98 (d, J=21), 117.21, 119.11, 120.45, 127.93 (d, J=8), 135.62, 136.21, 136.24, 145.06, 146.00, 151.62, 153.07, 162.49 (d, J=246), 168.79, 171.41, 174.46.

MS (%): 468 (parent+1, 100).

HRMS Calc'd. for $C_{26}H_{27}FNO_6$: C, 468.1822. Found: 468.1795.

EXAMPLE 20

({3-[4-(2,3-Dihydro-benzo[4,1]dioxin-5-yloxy)-phenoxy]-3-phenyl-propyl}-methyl-amino)-acetic Acid Prepared as in Example 1, in 61% yield, as a foam.

$^{13}$C-NMR ($\delta$, CDCl$_3$): 14.40, 29.63, 33.73, 41.79, 54.00, 59.06, 64.44, 64.64, 72.80, 78.21, 111.86, 112.51, 117.05, 119.20, 120.42, 126.03, 128.29, 129.07, 135.56, 140.50, 145.03, 146.19, 151.40, 153.39, 168.40, 171.37.

MS (%): 450 (parent+1, 100).

HRMS Calc'd. for $C_{26}H_{27}NO_6$: C, 450.1916. Found: 450.1911.

EXAMPLE 21

{[3-[4-(2,3-Dihydro-benzofuran-7-yloxy)-phenoxy]-3-(4-fluoro-phenyl)-propyl]-methyl-amino}-acetic Acid Prepared as in Example 1, in 26% yield, as a foam.

$^{13}$C-NMR ($\delta$, CDCl$_3$): 30.31, 33.91, 41.77, 53.92, 72.10, 112.50, 115.99 (d, J=22), 117.09, 118.70, 118.89, 120.27, 121.23, 127.83 (d, J=8), 129.71, 136.41, 140.86, 150.51, 151.59, 153.00, 162.55 (d, J=245).

MS (%): 452 (parent+1, 100).

HRMS Calc'd. for $C_{26}H_{27}FNO_5$: C, 452.1874. Found: 452.1879.

EXAMPLE 22

({3-[4-(2,3-Dihydro-benzofuran-7-yloxy)-phenoxy]-3-phenyl-propyl}-methyl-amino)-acetic Acid Prepared as in Example 1, in 21% yield, as a foam.

$^{13}$C-NMR ($\delta$, CDCl$_3$): 30.32, 33.72, 41.80, 54.02, 59.25, 72.08, 78.15, 117.02, 118.73, 118.82, 120.17, 121.19, 126.03, 128.24, 129.05, 129.66, 140.57, 140.98, 150.47, 150.48, 151.43, 153.22, 168.36, 171.36.

MS (%): 434 (parent+1, 100).

Anal. Calc'd. for $C_{26}H_{28}NO_5$: C, 434.1968. Found: 434.1950.

EXAMPLE 23

{[3-[4-(Benzofuran-4-yloxy)-phenoxy]-3-(4-fluoro-phenyl)-propyl]-methyl-amino}-acetic Acid Prepared as in Example 1, in 100% yield, as a foam.

$^{13}$C-NMR ($\delta$, CDCl$_3$): 33.62, 41.58, 53.87, 58.96, 104.22, 104.26, 106.71, 110.57, 116.03 (d, J=22), 117.36, 119.30, 120.36, 124.98, 127.93 (d, J=24), 136.24, 136.27, 144.34, 151.11, 151.34, 153.56, 156.84, 162.52 (d, J=245), 168.87.

MS (%): 450 (parent+1, 100).

Anal. Calc'd. for $C_{26}H_{24}FNO_5 \cdot 5/4H_2O$: C, 66.11; H, 5.66; N, 2.97. Found: C, 66.26; H, 5.45; N, 2.64.

EXAMPLE 24

({3-[4-(2,3-Dihydro-benzofuran-4-yloxy)-phenoxy]-3-phenyl-proyl}-methyl-amino)-acetic Acid Prepared as in Example 1, in 91% yield, as an amorphous solid.

$^{13}$C-NMR (δ, CDCl$_3$): 27.62, 33.77, 41.49, 53.69, 58.59, 71.74, 78.30, 104.55, 104.58, 109.91, 109.94, 116.71, 117.18, 120.03, 126.07, 128.28, 129.06, 129.17, 140.56, 150.69, 153.66, 154.60, 162.21, 168.80, 171.32.

MS (%): 434 (parent+1, 100).

Anal. Calc'd. for C$_{26}$H$_{27}$NO$_5$.5/4H$_2$O: C, 68.48; H, 6.52; N, 3.07. Found: C, 68.18; H, 6.50; N, 2.86.

EXAMPLE 25

{[3-[4-(2,3-Dihydro-benzofuran-4-yloxy)-phenoxy]-3-(4-fluoro-phenyl)-propyl]-methyl-amino}-acetic Acid Prepared as in Example 1, in 96% yield, as a foam.

$^{13}$C-NMR (δ, CDCl$_3$): 27.60, 29.65, 33.87, 41.49, 53.61, 58.68, 71.72, 104.61, 109.91, 115.97 (d, J=21), 116.76, 117.26, 120.02, 120.34, 127.90 (d, J=25), 129.19, 136.41, 150.83, 153.44, 154.51, 161.25, 162.47 (d, J=245), 169.04, 171.31.

MS (%): 452 (parent+1, 100).

Anal. Calc'd. for C$_{26}$H$_{26}$FNO$_5$.3/2H$_2$O: C, 65.26; H, 6.11; N, 2.93. Found: C, 65.07; H, 6.21; N, 2.75.

EXAMPLE 26

{[3-[4-(3,5-Bis-trifluoromethyl-phenoxy)-phenoxy]-3-(4-fluoro-phenyl)-propyl]-methyl-amino}-acetic Acid Prepared as in Example 1, in 68% yield, as a foam.

$^{13}$C-NMR (δ, CDCl$_3$): 33.91, 41.81, 53.96, 58.96, 116.16 (d, J=22), 117.28, 117.77, 121.50, 121.76, 124.47, 127.85, 133.24 (q, J=34), 135.96, 148.75, 154.79, 159.51, 162.63 (d, J=246), 168.64.

MS (%): 546 (parent+1, 100).

HRMS Calc'd. for C$_{26}$H$_{22}$F$_7$NO$_4$: 546.1516. Found: C, 546.1525.

EXAMPLE 27

({3-(4-Fluoro-phenyl)-3-[4-(4-trifluoromethoxy-phenoxy)-phenoxy]-propyl}-methylamino)-acetic Acid Prepared as in Example 1, in 95% yield, as a foam.

$^{13}$C-NMR (δ, CDCl$_3$): 33.71, 41.63, 53.92, 59.01, 116.08 (d, J=22), 117.38, 118.72, 120.67 (q, J=256), 120.83, 122.70, 127.84 (d, J=8), 136.14, 144.21, 150.55, 153.84, 156.76, 162.55 (d, J=246), 168.75.

MS (%): 494 (parent+1, 100).

HRMS Calc'd. for C$_{25}$H$_{23}$F$_4$NO$_5$: 494.1591. Found: 494.1591.

EXAMPLE 28

(Methyl-{3-phenyl-3-[4-(4-trifluoromethoxy-phenoxy)-phenoxy]-propyl}-amino)-acetic Acid Prepared as in Example 1, in 100% yield, as a foam.

$^{13}$C-NMR (δ, CDCl$_3$): 33.70, 41.63, 53.88, 58.77, 60.59, 78.16, 78.22, 117.31, 118.64, 120.68 (q, J=256), 120.84, 122.67, 126.01, 128.37, 129.12, 140.38, 144.14, 150.34, 154.13, 156.89, 168.66, 174.31.

MS (%): 476 (parent+1, 100).

HRMS Calc'd. for C$_{25}$H$_{24}$F$_3$NO$_5$: 476.1685. Found: 476.1683.

EXAMPLE 29

{[3-[4-(Benzo[1,3]dioxol-5-yloxy)-phenoxy]-3-(4-fluoro-phenyl)-propyl]-methyl-amino}-acetic Acid Prepared as in Example 1, in 90% yield, as a foam.

$^{13}$C-NMR (δ, CDCl$_3$): 33.63, 41.51, 53.82, 58.90, 77.63, 101.47, 101.53, 101.62, 108.35, 111.03, 111.07, 112.50, 116.00 (d, J=22), 117.24, 119.54, 127.87 (d, J=8), 136.29, 143.52, 148.46, 152.09, 152.48, 153.11, 162.48 (d, J=246), 168.75, 171.41.

MS (%): 454 (parent+1, 100).

Anal. Calc'd. for C$_{25}$H$_{24}$FNO$_6$.3/4H$_2$O: C, 64.30; H, 5.50; N, 3.00. Found: C, 64.27; H, 5.40; N, 2.83.

EXAMPLE 30

({3-[4-(Benzo[1,3]dioxol-5-yloxy)-phenoxy]-3-phenyl-propyl}-methyl-amino)-acetic Acid Prepared as in Example 1, in 66% yield, as a foam.

$^{13}$C-NMR (δ, CDCl$_3$): 33.73, 41.66, 53.87, 58.96, 78.19, 101.45, 101.52, 101.60, 108.34, 111.01, 117.11, 119.57, 126.02, 128.29, 129.08, 140.51, 143.46, 148.41, 148.45, 151.92, 152.62, 153.38, 168.43, 171.36.

MS (%): 436 (parent+1, 100).

HRMS Calc'd. for C$_{25}$H$_{26}$NO$_6$: 436.1760. Found: 436.1730.

EXAMPLE 31

({3-[4-(3-Methoxy-phenoxy)-phenoxy]-3-phenyl-propyl}-methyl-amino)-acetic Acid

Prepared as in Example 1, in 84% yield, as a foam.

$^{13}$C-NMR (δ, CDCl$_3$): 33.77, 41.53, 53.71, 55.48, 58.73, 78.20, 104.08, 108.32, 110.10, 117.19, 120.83, 126.05, 128.28, 129.08, 130.21, 140.60, 150.50, 153.93, 159.56, 161.04, 168.87.

MS (%): 422 (parent+1, 100).

HRMS Calc'd. for C$_{25}$H$_{28}$NO$_5$: 422.1968. Found: 422.1961.

EXAMPLE 32

({3-(4-Fluoro-phenyl)-3-[4-(3-methoxy-phenoxy)-phenoxy]-propyl}-methyl-amino)-acetic Acid Prepared as in Example 1, in 100% yield, as a foam.

$^{13}$C-NMR (δ, CDCl$_3$): 33.80, 41.58, 53.73, 55.47, 58.81, 77.65, 104.17, 108.32, 110.15, 116.00 (d, J=22), 117.25, 120.83, 127.85 (d, J=8), 130.23, 136.34, 150.69, 153.67, 159.47, 161.04, 162.55 (d, J=245), 168.85.

MS (%): 440 (parent+1, 100).

HRMS Calc'd. for C$_{25}$H$_{27}$FNO$_5$: 440.1874. Found: 440.1883.

EXAMPLE 33

(Methyl-{3-phenyl-3-[4-(3-trifluoromethoxy-phenoxy)-phenoxy]-propyl}-amino)-acetic Acid Prepared as in Example 1, in 84% yield, as a foam.

$^{13}$C-NMR (δ, CDCl$_3$): 33.69, 41.49, 53.72, 58.61, 60.52, 78.26, 110.51, 114.60, 115.65, 117.39, 119.26, 120.53 (q, 257), 121.14, 121.81, 126.04, 128.31, 129.07, 130.52, 140.47, 149.62, 150.20, 154.43, 159.61, 168.99, 171.28, 174.21.

MS (%): 476 (parent+1, 100).

HRMS Calc'd. for $C_{25}H_{25}F_3NO_5$: 476.1685. Found: 476.1682.

EXAMPLE 34

({3-(4-Fluoro-phenyl)-3-[4-(3-trifluoromethoxy-phenoxy)-phenoxy]-propyl}-methyl-amino)-acetic Acid Prepared as in Example 1, in 83% yield, as a foam.

$^{13}$C-NMR ($\delta$, CDCl$_3$): 33.77, 41.68, 53.92, 58.93, (1 signal missing in this region), 110.61, 114.76, 115.76, 116.11 (d, J=21), 117.43, 120.5 (q, J=257), 121.19, 123.29, 127.84 (d, J=8), 130.57, 136.13, 149.89, 150.26, 154.11, 159.52, 162.58 (d, J=245), 168.68.

MS (%): 494 (parent+1, 100).

HRMS Calc'd. for $C_{25}H_{24}F_4NO_5$: 496.1591. Found: 496.1600.

EXAMPLE 35

({3-[4-(2-Methoxy-phenoxy)-phenoxy]-3-phenyl-propyl}-methyl-amino)-acetic Acid

Prepared as in Example 1, in 95.5% yield, as a foam.

$^{13}$C-NMR ($\delta$, CDCl$_3$): 33.41, 41.79, 54.29, 56.11, 58.77, 78.13, 112.86, 117.13, 118.95, 120.04, 121.21, 124.39, 126.08, 128.34, 129.09, 140.41, 146.20, 151.13, 151.85, 153.12, 168.78, 175.05.

MS (%): 422 (parent+1, 100).

HRMS Calc'd. for $C_{25}H_{28}NO_5$: 422.1968. Found: 422.1961.

EXAMPLE 36

({3-(4-Fluoro-phenyl)-3-[4-(2-methoxy-phenoxy)-phenoxy]-propyl}-methyl-amino)-acetic Acid Prepared as in Example 1, in 90% yield, as a foam.

$^{13}$C-NMR ($\delta$, CDCl$_3$): 33.83, 41.70, 53.87, 56.13, 58.95, 112.84, 115.99 (d, J=22), 117.14, 118.98, 120.05, 121.21, 124.42, 127.88 (d, J=8), 136.40, 146.16, 151.14, 151.94, 153.01, 162.53 (d, J=245), 168.64.

MS (%): 440 (parent+1, 100).

HRMS Calc'd. for $C_{25}H_{27}FNO_5$: 440.1874. Found: 440.1863.

EXAMPLE 37

({3-[4-(3,4-Dimethoxy-phenoxy)-phenoxy]-3-phenyl-propyl}-methyl-amino)-acetic Acid Prepared as in Example 1, in 83% yield, as a foam.

$^{13}$C-NMR ($\delta$, CDCl$_3$): 33.74, 41.45, 53.63, 56.06, 56.09, 56.45, 56.48, 58.49, 78.23, 103.84, 109.80, 111.88, 117.16, 119.41, 126.07, 128.24, 129.04, 140.65, 145.18, 150.00, 151.63, 151.97, 153.33, 168.82.

MS (%): 452 (parent+1, 100).

HRMS Calc'd. for $C_{26}H_{30}NO_6$: 452.2073. Found: 452.2083.

EXAMPLE 38

{[3-[4-(3,4-Dimethoxy-phenoxy)-phenoxy]-3-(4-fluoro-phenyl)-propyl]-methyl-amino}-acetic Acid Prepared as in Example 1, in 85% yield, as a foam.

$^{13}$C-NMR ($\delta$, CDCl$_3$): 33.85, 41.54, 53.69, 56.08, 56.11, 56.45, 56.48, 58.71, 103.92, 109.86, 111.87, 115.99 (d, J=22), 117.21, 119.38, 127.88 (d, J=8), 136.44, 145.26, 150.03, 151.52, 152.19, 153.07, 162.49 (d, J=246), 168.84.

MS (%): 470 (parent+1, 100).

HRMS Calc'd. for $C_{26}H_{29}FNO_6$: 470.1979. Found: 470.1965.

EXAMPLE 39

({3-[4-(2,3-Dihydro-benzo[1,4]dioxin-6-yloxy)-phenoxy]-3-phenyl-propyl}-methyl-amino)-acetic Acid Prepared as in Example 1, in 70% yield, as a foam.

$^{13}$C-NMR ($\delta$, CDCl$_3$): 29.66, 33.56, 41.64, 53.90, 59.02, 64.32, 64.65, 78.15, 107.84, 111.76, 117.15, 117.75, 119.78, 126.08, 128.27, 129.08, 139.55, 140.64, 144.06, 151.73, 151.97, 153.42, 168.88, 171.39.

MS (%): 450 (parent+1, 100).

HRMS Calc'd. for $C_{26}H_{28}NO_6$: 450.1917. Found: 450.1905.

EXAMPLE 40

{[3-[4-(2,3-Dihydro-benzo[1,4]dioxin-6-yloxy)-phenoxy]-3-(4-fluoro-phenyl)-propyl]-methyl-amino}-acetic Acid Prepared as in Example 1, in 79% yield, as a foam.

$^{13}$C-NMR ($\delta$, CDCl$_3$): 29.65, 33.88, 41.54, 53.66, 58.67, 64.30, 64.64, 77.70, 107.88, 111.78, 116.01 (d, J=22), 117.19, 117.77, 119.75, 127.86 (d, J=8), 136.42, 136.45, 139.60, 144.07, 151.86, 151.89, 153.20, 161.49 (d, J=246), 168.85.

MS (%): 468 (parent+1, 100).

HRMS Calc'd. for $C_{26}H_{27}FNO_6$: 468.1822. Found: 468.1829.

EXAMPLE 41

{Methyl-[3-(3-methyl-4-p-tolyloxy-phenoxy)-3-phenyl-propyl]-amino}-acetic Acid

Prepared as in Example 1, in 100% yield, as a foam.

MS (%): 420 (parent+1, 100).

EXAMPLE 42

({3-(4-Fluoro-phenyl)-3-[4-(4-methoxy-phenoxy)-3-methyl-phenoxy]-propyl}-methyl-amino)-acetic Acid Prepared as in Example 1, in 100% yield, as a foam.

$^{13}$C-NMR ($\delta$, CDCl$_3$): 16.60, 33.72, 41.71, 54.02, 55.85, 58.89, 77.58, 114.02, 114.88, 116.02 (d, J=22), 118.34, 119.00, 120.09, 127.78 (d, J=8), 131.07, 136.34, 149.65, 152.00, 153.29, 155.07, 162.52 (d, J=245), 168.50.

MS (%): 454 (parent+1, 100).

HRMS Calc'd. for $C_{26}H_{29}FNO_5$: 454.2030. Found: 454.2018.

EXAMPLE 43

{[3-[4-(Benzo[1,3]dioxol-5-yloxy)-phenoxy]-3-(4-chloro-phenyl)-propyl]-methyl-amino}-acetic Acid Prepared as in Example 1, in 70.5% yield, as a foam.

$^{13}$C-NMR ($\delta$, CDCl$_3$): 33.75, 41.58, 53.63, 58.77, 60.57, 77.63, 101.53, 101.62, 108.35, 111.08, 117.12, 119.55, 127.53, 129.25, 133.95, 139.19, 143.53, 148.46, 152.13, 152.49, 153.09, 168.83.

MS (%): 470 (parent+1, 100).

HRMS Calc'd. for $C_{25}H_{25}ClNO_6$: 470.1370. Found: 470.1370.

EXAMPLE 44

{[3-[4-(3-Methoxy-phenoxy)-phenoxy]-3-(4-methoxy-phenyl)-propyl]-methyl-amino}-acetic Acid Prepared as in Example 1, in 80% yield, as a foam.

$^{13}$C-NMR (δ, CDCl$_3$): 33.58, 41.70, 54.03, 55.44, 55.51, 58.95, 77.83, 104.09, 108.30, 110.12, 114.47, 117.31, 120.82, 127.35, 130.21, 132.26, 150.50, 153.83, 159.53, 159.57, 161.02, 168.45.

MS (%): 452 (parent+1, 100).

HRMS Calc'd. for $C_{26}H_{30}NO6$: 452.2073. Found: 452.2061.

EXAMPLE 45

({3-(4-Chloro-phenyl)-3-[4-(3-methoxy-phenoxy)-phenoxy]-propyl}-methyl-amino)-acetic Acid Prepared as in Example 1, in 100% yield, as a foam.

$^{13}$C-NMR (δ, CDCl$_3$): 33.77, 41.62, 53.70, 55.50, 58.81, 77.62, 104.20, 108.35, 110.18, 117.18, 120.85, 127.55, 129.29, 130.24, 134.00, 139.13, 150.74, 153.60, 159.45, 161.05, 168.78.

MS (%): 456 (parent+1, 100).

HRMS Calc'd. for $C_{26}H_{27}ClNO_5$: 456.1578. Found: 456.1578.

EXAMPLE 46

{[3-[4-(4-Methoxy-phenoxy)-phenoxy]-3-(4-methoxy-phenyl)-propyl]-methyl-amino}-acetic Acid Prepared as in Example 1, in 89% yield, as a foam.

$^{13}$C-NMR (δ, CDCl$_3$): 33.59, 41.68, 53.99, 55.43, 55.84, 59.02, 77.86, 114.44, 114.93, 117.25, 119.28, 120.01, 127.34, 132.37, 151.27, 152.26, 153.14, 155.62, 159.49, 168.43.

MS (%): 452 (parent+1, 100).

HRMS Calc'd. for $C_{26}H_{30}NO_6$: 452.2073. Found: 452.2075.

EXAMPLE 47

({3-(4-Chloro-phenyl)-3-[4-(4-methoxy-phenoxy)-phenoxy]-propyl}-methyl-amino)-acetic Acid Prepared as in Example 1, in 92% yield, as a foam.

$^{13}$C-NMR (δ, CDCl$_3$): 33.73, 41.70, 53.80, 55.84, 58.92, 77.58, 114.96, 117.11, 119.27, 120.11, 127.53, 129.28, 133.99, 139.14, 151.13, 152.55, 152.84, 155.71, 168.57.

MS (%): 456 (parent+1, 100).

HRMS Calc'd. for $C_{25}H_{27}ClNO_5$: 456.1578. Found: 456.1580.

EXAMPLE 48

{[3-[2-Chloro-4-(4-methoxy-phenoxy)-phenoxy]-3-(4-fluoro-phenyl)-propyl]-methyl-amino}-acetic Acid Prepared as in Example 1, in 89% yield, as a foam.

$^{13}$C-NMR (δ, CDCl$_3$): 33.65, 41.54, 53.70, 55.71, 58.83, 60.52, 69.70, 78.85, 115.03, 115.93 (d, J=22), 116.82, 117.00, 119.77, 120.55, 124.16, 128.01 (d, J=8), 135.87, 135.89, 148.37, 150.16, 152.84, 156.10, 162.57 (d, J=245), 168.92, 171.29.

MS (%): 474 (parent+1, 100).

HRMS Calc'd. for $C_{25}H_{26}ClFNO_5$: 474.1485. Found: 474.1500.

EXAMPLE 49

{[3-(4-Fluoro-phenyl)-3-(3-methyl-4-phenoxy-phenoxy)-propyl]-methyl-amino}-acetic Acid Prepared as in Example 1, in 100% yield, as a foam.

$^{13}$C-NMR (δ, CDCl$_3$): 29.64, 33.91, 41.63, 53.84, 58.75, 77.59, 114.19, 116.04 (d, J=22), 116.56, 118.99, 121.53, 122.11, 127.78 (d, J=8), 129.76, 131.83, 136.40, 148.28, 153.94, 158.58, 162.52 (d, J=246), 168.64.

MS (%): 424 (parent+1, 100).

HRMS Calc'd. for $C_{25}H_{27}FNO_4$: 424.1924. Found: 424.1910.

EXAMPLE 50

{[3-[4-(Benzo[1,3]dioxol-5-yloxy)-phenoxy]-3-(4-methoxy-phenyl)-propyl]-methyl-amino}-acetic Acid Prepared as in Example 1, in 100% yield, as a foam.

$^{13}$C-NMR (δ, CDCl$_3$): 29.62, 29.89, 33.53, 41.67, 54.01, 55.42, 58.95, 77.84, 101.48, 101.60, 108.33, 110.99, 114.45, 117.29, 119.57, 127.36, 132.31, 143.45, 148.44, 151.89, 152.64, 153.34, 159.50, 168.53.

MS (%): 466 (parent+1, 100).

HRMS Calc'd. for $C_{26}H_{28}NO_7$: 466.1866. Found: 466.1854.

EXAMPLE 51

{[3-[2-Chloro-4-(4-methoxy-phenoxy)-phenoxy]-3-(4-methoxy-phenyl)-propyl]-methyl-amino}-acetic Acid Prepared as in Example 1, in 90% yield, as a foam.

$^{13}$C-NMR (δ, CDCl$_3$): 33.50, 41.62, 53.97, 55.39, 55.42, 55.81, 58.99, 79.20, 114.43, 115.05, 116.93, 117.19, 119.82, 120.54, 124.19, 127.52, 131.81, 148.58, 150.33, 152.70, 156.07, 159.66, 168.62.

MS (%): 486 (parent+1, 100).

EXAMPLE 52

{[3-[3-Methoxy-4-(4-methoxy-phenoxy)-phenoxy]-3-(4-methoxy-phenyl)-propyl]-methyl-amino}-acetic Acid Prepared as in Example 1, in 93% yield, as a foam.

$^{13}$C-NMR (δ, CDCl$_3$): 29.65, 33.66, 41.92, 54.18, 55.49, 55.86, 56.20, 77.79, 102.52, 106.93, 114.54, 114.76, 118.34, 120.70, 127.31, 132.28, 140.29, 143.47, 151.98, 152.08, 154.45, 155.16, 159.61, 168.20.

MS (%): 482 (parent+1, 100).

HRMS Calc'd. for $C_{27}H_{32}NO_7$: 482.2179. Found: 482.2188.

EXAMPLE 53

({3-(4-Fluoro-phenyl)-3-[3-methoxy-4-(3-methoxy-phenoxy)-phenoxy]-propyl}-methyl-amino)-acetic Acid Prepared as in Example 1, in 93% yield, as a foam.

$^{13}$C-NMR (δ, CDCl$_3$): 33.50, 41.54, 53.94, 55.47, 56.17, 58.98, 60.65, 77.67, 102.62, 102.77, 107.11, 107.62, 108.62, 116.09 (d, J=22), 122.43, 127.94 (d, J=8), 130.08, 136.30, 136.33, 138.57, 152.61, 155.04, 159.96, 160.96, 162.55 (d, J=246), 168.93.

MS (%): 470 (parent+1, 100).

HRMS Calc'd. for $C_{26}H_{29}FNO_6$: 470.1979. Found: 470.1987.

EXAMPLE 54

({3-(4-Fluoro-phenyl)-3-[3-methoxy-4-(4-methoxy-phenoxy)-phenoxy]-propyl}-methyl-amino)-acetic Acid Prepared as in Example 1, in 100% yield, as a foam.

$^{13}$C-NMR ($\delta$, CDCl$_3$): 33.73, 41.61, 53.78, 55.79, 56.14, 58.82, 60.57, 77.62, 102.43, 106.75, 114.73, 116.04 (d, J=21), 118.31, 120.65, 127.79 (d, J=8), 136.36, 140.39, 151.96, 154.26, 155.16, 162.57 (d, J=246), 168.70.

MS (%): 470 (parent+1, 100).

HRMS Calc'd. for $C_{26}H_{29}FNO_6$: 470.1979. Found: 470.2000.

EXAMPLE 55

({3-[3-Methoxy-4-(3-methoxy-phenoxy)-phenoxy]-3-phenyl-propyl}-methyl-amino)-acetic Acid Prepared as in Example 1, in 99% yield, as a foam.

$^{13}$C-NMR ($\delta$, CDCl$_3$): 33.44, 41.56, 53.99, 55.45, 56.13, 58.95, 60.63, 78.07, 102.51, 102.69, 107.08, 107.64, 108.58, 122.39, 126.07, 128.38, 129.14, 130.02, 138.39, 140.50, 152.52, 155.24, 160.01, 160.92, 168.87.

MS (%): 452 (parent+1, 100).

HRMS Calc'd. for $C_{26}H_{30}NO_6$: 452.2073. Found: 452.2073.

EXAMPLE 56

({3-[3-Methoxy-4-(4-methoxy-phenoxy)-phenoxy]-3-phenyl-propyl}-methyl-amino)-acetic Acid Prepared as in Example 1, in 100% yield, as a solid, mp 60.1° C.

$^{13}$C-NMR ($\delta$, CDCl$_3$): 33.47, 41.56, 53.97, 55.84, 56.16, 58.97, 60.64, 78.08, 102.49, 106.90, 114.76, 118.28, 120.76, 126.07, 128.37, 129.13, 140.22, 140.56, 151.99, 152.06, 154.50, 155.12, 168.76.

MS (%): 452 (parent+1, 100).

HRMS Calc'd. for $C_{26}H_{30}NO_6$: 452.2073. Found: 452.2081.

EXAMPLE 57

({3-[4-(3-Methoxy-phenoxy)-2-methyl-phenoxy]-3-phenyl-propyl}-methyl-amino)-acetic Acid Prepared as in Example 1, in 92% yield, as a foam.

$^{13}$C-NMR ($\delta$, CDCl$_3$): 16.92, 29.65, 33.53, 41.57, 54.01, 55.53, 58.71, 104.07, 108.16, 110.11, 113.93, 117.71, 122.54, 125.98, 128.36, 128.64, 129.12, 130.18, 140.49, 149.93, 151.82, 159.73, 161.02, 168.59.

MS (%): 436 (parent+1, 100).

HRMS Calc'd. for $C_{26}H_{30}NO_5$: 436.2124. Found: 436.2103.

EXAMPLE 58

{[3-[3-Methoxy-4-(3-methoxy-phenoxy)-phenoxy]-3-(4-methoxy-phenyl)-propyl]-methyl-amino}-acetic Acid Prepared as in Example 1, in 100% yield, as a foam.

$^{13}$C-NMR ($\delta$, CDCl$_3$): 29.65, 33.51, 41.69, 54.08, 55.49, 56.16, 58.91, 77.77, 102.55, 102.72, 107.14, 107.64, 108.63, 114.54, 122.38, 127.35, 130.03, 132.29, 138.39, 152.51, 155.23, 159.60, 160.04, 160.93, 168.51.

MS (%): 482 (parent+1, 100).

HRMS Calc'd. for $C_{27}H_{32}NO_7$: 482.2179. Found: 482.2187.

EXAMPLE 59

{[3-(3-Methoxy-4-phenoxy-phenoxy)-3-phenyl-propyl]-methyl-amino}-acetic Acid

Prepared as in Example 1, in 98% yield, as a solid, mp 77.5° C.

$^{13}$C-NMR ($\delta$, CDCl$_3$): 29.64, 33.48, 41.57, 53.95, 56.10, 58.95, 78.07, 102.46, 107.02, 116.42, 122.16, 126.03, 128.38, 129.13, 129.59, 138.67, 140.51, 152.49, 155.12, 158.68, 168.75.

MS (%): 422 (parent+1, 100).

HRMS Calc'd. for $C_{25}H_{28}NO_5$: 422.1968. Found: 422.1972.

EXAMPLE 60

{[3-(4-Fluoro-phenyl)-3-(3-methoxy-4-phenoxy-phenoxy)-propyl]-methyl-amino}-acetic Acid Prepared as in Example 1, in 100% yield, as a solid, mp 139.5° C.

$^{13}$C-NMR ($\delta$, CDCl$_3$): 33.79, 41.65, 53.80, 56.11, 58.83, 60.59, 77.61, 102.46, 106.90, 116.08 (d, J=22), 116.44, 122.15, 122.22, 127.79 (d, J=8), 129.60, 136.31, 136.34, 138.85, 152.53, 154.89, 158.63, 162.55 (d, J=246), 168.67, 171.37.

MS (%): 440 (parent+1, 100).

HRMS Calc'd. for $C_{25}H_{27}FNO_5$: 440.1874. Found: 440.1876.

EXAMPLE 61

{[3-(4-Fluoro-phenyl)-3-(2-methyl-4-phenoxy-phenoxy)-propyl]-methyl-amino}-acetic Acid Prepared as in Example 1, in 100% yield, as a foam.

$^{13}$C-NMR ($\delta$, CDCl$_3$): 16.90, 33.55, 41.48, 42.16, 53.93, 58.69, 65.37, 77.00, 114.06, 116.10 (d, J=22), 117.50, 118.02, 122.37, 122.78, 127.84 (d, J=7), 128.72, 129.81, 136.35, 150.38, 151.49, 158.33, 162.55 (d, J=246), 168.76.

MS (%): 424 (parent+1, 100).

EXAMPLE 62

{Methyl-[3-(2-methyl-4-phenoxy-phenoxy)-3-phenyl-propyl]-amino}-acetic Acid

Prepared as in Example 1, in 100% yield, as a foam.

$^{13}$C-NMR ($\delta$, CDCl$_3$): 16.94, 33.65, 41.46, 53.83, 58.79, 113.95, 117.54, 117.98, 122.38, 122.67, 126.00, 128.33, 128.68, 129.11, 129.79, 140.66, 150.19, 151.81, 158.46, 168.78.

MS (%): 406 (parent+1, 100).

EXAMPLE 63

({3-[4-(4-Methoxy-phenoxy)-2-methyl-phenoxy]-3-phenyl-propyl}-methyl-amino)-acetic Acid Prepared as in Example 1, in 98% yield, as a foam.

$^{13}$C-NMR ($\delta$, CDCl$_3$): 16.96, 29.65, 33.63, 41.76, 54.14, 55.86, 59.03, 112.50, 113.89, 114.91, 116.12, 119.99, 121.12, 125.97, 128.34, 128.51, 129.12, 139.92, 140.54, 151.12, 151.42, 151.72, 155.57.

MS (%): 436 (parent+1, 100).

EXAMPLE 64

({3-[4-(4-Chloro-phenoxy)-2-methyl-phenoxy]-3-phenyl-propyl}-methyl-amino)-acetic Acid Prepared as in Example 1, in 100% yield, as a foam.

$^{13}$C-NMR ($\delta$, CDCl$_3$): 16.94, 33.54, 41.47, 53.90, 58.90, 114.01, 117.58, 119.12, 122.36, 126.00, 127.53, 128.36, 128.82, 129.12, 129.70, 140.54, 149.82, 152.01, 157.14, 168.88.

MS (%): 440 (parent+1, 100).

EXAMPLE 65

{Methyl-[3-(2-methyl-4-p-tolyloxy-phenoxy)-3-phenyl-propyl]-amino}-acetic Acid

Prepared as in Example 1, in 100% yield, as a foam.

$^{13}$C-NMR ($\delta$, CDCl$_3$): 16.94, 20.85, 33.55, 41.43, 53.87, 58.85, 113.97, 116.99, 118.24, 121.85, 126.05, 128.29, 128.57, 129.09, 130.28, 132.27, 140.71, 150.83, 151.51, 155.98, 168.90.

MS (%): 420 (parent+1, 100).

EXAMPLE 66

{[3-(2-Chloro-4-phenoxy-phenoxy)-3-(4-fluoro-phenyl)-propyl]-methyl-amino}-acetic Acid Prepared as in Example 1, in 88.5% yield, as a foam.

$^{13}$C-NMR ($\delta$, CDCl$_3$): 33.74, 41.50, 53.62, 58.83, 78.85, 116.01 (d, J=21), 116.91, 118.20, 118.56, 121.19, 123.55, 124.21, 127.99 (d, J=8), 129.96, 135.82, 135.85, 149.02, 151.38, 157.29, 162.55 (d,J=246), 169.03, 171.28, MS (%): 444 (parent+1, 100).

EXAMPLE 67

{[3-(2-Chloro-4-p-tolyloxy-phenoxy)-3-(4-fluoro-phenyl)-propyl]-methyl-amino}-acetic Acid Prepared as in Example 1, in 100% yield, as a solid, mp 129.3° C.

$^{13}$C-NMR ($\delta$, CDCl$_3$): 14.39, 33.58, 41.53, 53.70, 58.56, 78.85, 116.02 (d, J=21), 117.01, 117.65, 118.86, 120.58, 124.17, 128.04 (d, J=8), 130.48, 133.29, 135.78, 135.81, 148.64, 152.13, 154.78, 162.62 (d, J=246), 168.84.

MS (%): 458 (parent+1, 100).

EXAMPLE 68

{[3-[2-Chloro-4-(4-chloro-phenoxy)-phenoxy]-3-(4-fluoro-phenyl)-propyl]-methyl-amino}-acetic Acid Prepared as in Example 1, in 100% yield, as a foam.

$^{13}$C-NMR ($\delta$, CDCl$_3$): 33.75, 41.60, 53.75, 58.70, 78.86, 116.11 (d, J=21), 116.92, 118.31, 119.77, 121.33, 124.36, 127.98 (d, J=9), 128.56, 129.96, 135.66, 149.32, 151.00, 156.05, 162.68 (d, J=246), 168.81.

MS (%): 479 (parent+1, 100).

EXAMPLE 69

{Methyl-[3-(3-phenoxy-phenoxy)-3-phenyl-propyl]-amino}-acetic Acid

Prepared as in Example 1, in 95% yield, as a foam.

$^{13}$C-NMR ($\delta$, CDCl$_3$): 33.56, 41.45, 53.63, 58.52, 77.03, 77.36, 77.67, 106.79, 110.83, 111.38, 119.34, 123.65, 126.01, 128.25, 129.08, 129.95, 130.29, 140.26, 156.74, 158.49, 158.84, 168.75.

MS (%): 392 (parent+1, 100).

HRMS Calc'd. for C$_{24}$H$_{26}$NO$_4$: 392.1862. Found: 392.1866.

EXAMPLE 70

{[3-(4-Fluoro-phenyl)-3-(3-phenoxy-phenoxy)-propyl]-methyl-amino}-acetic Acid

Prepared as in Example 1, in 75% yield, as a foam.

$^{13}$C-NMR ($\delta$, CDCl$_3$): 33.70, 41.59, 53.69, 58.84, 60.61, 76.95, 77.05, 77.27, 77.59, 106.75, 110.81, 111.51, 116.02 (d, J=22), 119.39, 123.74, 127.79 (d, J=8), 129.95, 130.33, 136.08, 156.69, 158.61, 162.49 (d, J=246), 168.70, 171.37.

MS (%): 410 (parent+1, 100).

HRMS Calc'd. for C$_{24}$H$_{25}$FNO$_4$: 410.1768. Found: 410.1788.

EXAMPLE 71

{[3-(4-Fluoro-phenyl)-3-(3-p-tolyloxy-phenoxy)-propyl]-methyl-amino}-acetic Acid A. 3-(4-Tolyl)oxy-phenol O-benzyl ether Following Scheme II: To a 50 mL round-bottomed flask equipped with gas inlet and reflux condenser were added 800 mg (4.0 mmol) 3-benzyloxyphenol, 1.1 g (8.0 mmol) 4-tolyl boronic acid, 726 mg (4.0 mmol) cupric acetate, 1.6 mL (20 mmol) dry pyridine, 900 mg molecular sieves, and 10 mL dry dimethylsulfoxide. The reaction was stirred under an atmosphere of dry oxygen at room temperature for 24 hr. The reaction was then taken up in ethyl acetate, washed with several portions of water, washed with brine, dried over sodium sulfate, and evaporated. The residue was chromatographed on silica gel using hexane/ethyl acetate as eluant to afford 602 mg (52%) of the product as an oil.

$^1$H-NMR ($\delta$, CDCl$_3$): 2.3 (s, 3H), 5.00 (m, 2H), 6.4–6.7 (m, 3H), (6.8-7.4 (m, 10H), MS (%): 291 (parent+1, 100).

B. 3-(4-Tolyloxy)-phenol

Following Scheme II: To a 50 mL round-bottomed flask equipped with reflux condenser and N$_2$ inlet were added 602 mg (2.07 mmol) 3-(4-tolyloxy)-phenol-O-benzyl ether, 600 mg (15 mmol) ammonium formate, 200 mg 20% palladium hydroxide on carbon, and 20 mL ethanol. The reaction was reflxued for 1 hr, cooled, and filtered through Celite with ethanol. The filtrate was concentrated and the residue chromatographed on silica gel using hexane/ethyl acetate as eluant to afford 185 mg (45%) of the product as an oil.

$^1$H-NMR ($\delta$, CDCl$_3$): 2.33 (s, 3H), 6.45 (t, J=2, 1H), 6.53 (m, 2H), 6.94 (m, 2H), 7.13 (m, 3H).

$^{13}$C-NMR ($\delta$, CDCl$_3$): 20.96, 105.70, 110.04, 110.69, 119.765, 130.52, 130.60, 133.56, 154.37, 156.94, 159.47.

GC MS (%): 200 (parent, 100).

The remaining steps were carried out as in Example 1 to afford the final product, with in 100% yield in the final step, as a foam.

$^{13}$C-NMR ($\delta$, CDCl$_3$): 20.94, 33.67, 41.54, 42.17, 53.71, 58.46, 65.38, 106.29, 110.42, 111.02, 116.01 (d, J=21), 119.64, 127.81 (d, J=8), 130.26, 130.48, 133.47, 136.06, 136.09, 154.18, 158.59, 159.23, 162.49 (d, J=246), 168.62.

MS (%): 424 (parent+1, 100).

HRMS Calc'd. for $C_{25}H_{27}FNO_4$: 424.1924. Found: 424.1917.

EXAMPLE 72

({3-(4-Fluoro-phenyl)-3-[3-(4-methoxy-phenoxy)-phenoxy]-propyl}-methyl-amino)-acetic Acid Prepared as in Example 71, in 100% yield, as a foam.

$^{13}$C-NMR (δ, $CDCl_3$): 29.65, 33.52, 41.56, 53.83, 55.82, 58.49, 65.41, 105.61, 110.07, 110.36, 115.05, 116.01 (d, J=21), 121.29, 127.81 (d, J=8), 130.24, 136.03, 149.58, 156.26, 158.55, 159.88, 162.48 (d, J=246), 168.6.

MS (%): 440 (parent+1, 100).

HRMS Calc'd. for $C_{25}H_{27}FNO_5$: 440.1873. Found: 440.1856.

EXAMPLE 73

({3-[3-(4-Chloro-phenoxy)-phenoxy]-3-phenyl-propyl}-methyl-amino)-acetic Acid

Prepared as in Example 71, in 90% yield, as a foam.

$^{13}$C-NMR (δ, $CDCl_3$): 33.68, 41.45, 53.59, 58.57, 60.59, 77.74, 106.78, 111.24, 111.38, 117.46, 120.56, 125.97, 128.29, 128.58, 129.09, 129.43, 129.90, 130.40, 140.22, 155.45, 158.14, 158.88, 168.75.

MS (%): 426 (parent+1, 100).

HRMS Calc'd. for $C_{24}H_{25}ClNO_4$: 426.1472. Found: 426.1476.

EXAMPLE 74

{[3-[3-(4-Chloro-phenoxy)-phenoxy]-3-(4-fluoro-phenyl)-propyl]-methyl-amino}-acetic Acid Prepared as in Example 71, in 77% yield, as a foam.

$^{13}$C-NMR (δ, $CDCl_3$): 33.80, 41.61, 53.70, 58.78, 60.59, 77.57, 106.73, 111.14, 111.50, 116.06 (d, J=22), 117.48, 120.65, 127.75 (d, J=8), 128.76, 129.50, 129.92, 130.45, 135.96, 155.37, 158.28, 158.65, 162.52 (d, J=245), 168.62, 171.36.

MS (%): 444 (parent+1, 100).

HRMS Calc'd. for $C_{24}H_{24}ClFNO_4$: 444.1370. Found: 444.1355.

EXAMPLE 75

({3-(4-Fluoro-phenyl)-3-[3-(2-methoxy-phenoxy)-phenoxy]-propyl}-methyl-amino)-acetic Acid Prepared as in Example 71, in 53% yield, as a foam.

$^{13}$C-NMR (δ, $CDCl_3$): 33.79, 41.02, 53.94, 56.04, 58.86, 60.60, 105.03, 109.98, 110.14, 112.99, 116.00 (d, J=21), 121.30, 121.71, 127.74 (d, J=8), 130.12, 136.05, 143.48, 144.47, 11.65, 158.50, 159.33, 162.47 (d, J=245), 168.35.

MS (%): 440 (parent+1, 100).

HRMS Calc'd. for $C_{25}H_{27}FNO_5$: 440.1873. Found: 440.1852.

EXAMPLE 76

{[3-(4-Fluoro-phenyl)-3-(4-methyl-3-phenoxy-phenoxy)-propyl]-methyl-amino}-acetic Acid Prepared as in Example 71, in 100% yield, as a foam.

$^{13}$C-NMR (δ, $CDCl_3$): 33.32, 41.62, 53.95, 58.53, 60.64, 77.69, 107.92, 111.70, 116.01 (J=21), 117.79, 122.57, 122.87, 127.92 (d, J=8), 129.91, 131.84, 135.99, 136.02, 155.18, 156.34, 157.46, 162.49 (d, J=246), 168.72, 171.44, 174.59.

MS (%): 424 (parent+1, 100).

HRMS Calc'd. for $C_{25}H_{27}FNO_4$: 424.1924. Found: 424.1941.

EXAMPLE 77

({3-(4-Fluoro-phenyl)-3-[3-(3-methoxy-phenoxy)-4-methyl-phenoxy]-propyl}-methyl-amino)-acetic Acid Prepared as in Example 71, in 100% yield, as a solid, mp 55–57° C.

$^{13}$C-NMR (δ, $CDCl_3$): 15.49, 33.40, 41.47, 53.77, 55.45, 58.90, 77.61, 103.92, 108.09, 108.33, 109.88, 111.87, 115.93 (d, J=22), 122.58, 127.89 (d, J=8), 130.28, 131.81, 136.06, 154.95, 156.37, 158.68, 161.09, 162.43 (d, J=246), 168.72.

MS (%): 454 (parent+1, 100).

EXAMPLE 78

({3-(4-Fluoro-phenyl)-3-[3-(4-methoxy-phenoxy)-4-methyl-phenoxy]-propyl}-methyl-amino)-acetic Acid Prepared as in Example 71, in 100% yield, as a solid, mp 63–65° C.

$^{13}$C-NMR (δ, $CDCl_3$): 15.55, 33.35, 41.38, 53.73, 55.78, 58.85, 77.01, 106.18, 110.46, 114.96, 115.87 (d, J=22), 119.91, 121.44, 127.87 (d, J=8), 131.60, 136.17, 136.20, 150.44, 155.66, 156.31, 156.62, 162.36 (d, J=245), 168.76.

MS (%): 454 (parent+1, 100).

EXAMPLE 79

{[3-[3-(Benzo[1,3]dioxol-5-yloxy)-4-methyl-phenoxy]-3-(4-fluoro-phenyl)-propyl]-methyl-amino}-acetic Acid Prepared as in Example 71, in 100% yield, as a solid, mp 185–188° C.

$^{13}$C-NMR (δ, $CDCl_3$): 15.49, 33.59, 41.48, 53.67, 58.73, 60.59, 76.98, 101.38, 101.66, 106.41, 108.35, 110.75, 110.93, 115.90 (d, J=21), 121.54, 127.80 (d, J=8), 131.61, 136.13, 136.16, 143.55, 148.49, 151.75, 156.32, 162.43 (d, J=246), 168.63.

MS (%): 468 (parent+1, 100).

EXAMPLE 80

({3-(4-Fluoro-phenyl)-3-[4-(pyridin-2-yloxy)-phenoxy]-propyl}-methyl-amino)-acetic Acid A. 4-(Pyridin-2-yloxy)-benzaldehyde Following Scheme I: Prepared as in Example 1 in 11.5% yield as an oil.

$^1$H-NMR (δ, $CDCl_3$): 6.99 (dd, J=1,8, 1H), 7.06 (m, 1H), 7.25 (m, 2H), 7.75 (m, 1H), 7.89 (m, 2H), 8.21 (m, 1H), 9.95 (s, 1H).

MS (%): 200 (parent+1, 100).

B. 4-(Pyridin-2-yloxy)-phenol

Following Scheme I: To a 100 mL round-bottomed flask equipped with condenser and $N_2$ inlet were added 3.1 g (50.2 mmol) boric acid, 10 mL tetrahydrofuran, 2.3 mL (20 mmol) 30% hydrogen peroxide, and 1 mL concentrated sulfuric acid. To the reaction was added a solution of 2.0 g (10 mmol) 4-(pyridin-2-yloxy)-benzaldehyde in 10 mL tetrahydrofuran dropwise over 5 minutes. The reaction was stirred 3 hr at 60° C., cooled, filtered, and the filtrate neutralized with saturated aqueous sodium bicarbonate solution. The mixture was extracted into 2× ethyl acetate, and the organic layer washed with brine, dried over sodium sulfate, and evaporated. The residue was chromatographed on silica gel using hexane/ethyl acetate as eluant to afford 180 mg (9.6%) of the product as a solid.

$^1$H-NMR (δ, CDCl$_3$): 6.72 (d, J=9, 2H), 6.87 (d, J=9, 2H), 6.9 (m, 1H), 6.97 (m, 1H), 7.65 (m, 1H), 8.15 (m, 1H).

$^{13}$C-NMR (δ, CDCl$_3$): 111.55, 117.17, 118.46, 122.38, 140,285, 146.78, 147.21, 153.96, 164.55.

MS (%): 188 (parent+1, 100).

The remaining steps were carried out as in Example 1 with an 81% yield in the final step, as a foam.

$^{13}$C-NMR (δ, CDCl$_3$): 33.60, 41.57, 53.85, 58.02, 111.42, 116.00 (d, J=22), 117.02, 118.48, 122.38, 127.89, (d, J=9), 136.26, 136.23, 139.60, 147.67, 148.06, 154.27, 162.49 (d, J=245), 164.04, 168.61.

MS (%): 411 (parent+1, 100).

HRMS Calc'd. for $C_{23}H_{24}FN_2O_4$: 411.1720. Found: 411.1747.

EXAMPLE 81

(Metyhl-{3-phenyl-3-[4-(pyridin-3-yloxy)-phenoxy]-propyl}-amino)-acetic Acid

Prepared as in Example 80, in 39% yield, as a foam.

$^{13}$C-NMR (δ, CDCl$_3$): 33.75, 41.69, 53.88, 58.49, 78.18, 117.45, 120.78, 124.24, 124.64, 126.03, 128.43, 129.16, 140.28, 140.57, 143.81, 149.83, 154.32, 154.92, 168.58.

MS (%): 393 (parent+1, 100).

HRMS Calc'd. for $C_{23}H_{25}N_2O_4$: 393.1814. Found: 393.1804.

EXAMPLE 82

(Methyl-{3-phenyl-3-[4-(pyridin-4-yloxy)-phenoxy]-propyl}-amino)-acetic Acid

Prepared as in Example 80, in 34% yield, as a foam.

$^{13}$C-NMR (δ, CDCl$_3$): 33.82, 41.77, 53.93, 59.03, 78.22, 111.93, 117.45, 122.10, 126.00, 128.42, 129.15, 140.31, 147.63, 151.14, 155.17, 165.54, 169.02.

MS (%): 393 (parent+1, 100).

EXAMPLE 83

({3-(4-Fluoro-phenyl)-3-[4-(pyridin-3-yloxy)-phenoxy]-propyl}-methyl-amino)-acetic Acid Prepared as in Example 80, in 65% yield, as a foam.

$^{13}$C-NMR (δ, CDCl$_3$): 33.70, 41.79, 53.99, 59.06, 60.59, 116.08 (d, J=21), 117.46, 120.76, 124.27, 124.77, 127.83 (d, J=8), 136.07, 140.44, 143.76, 149.95, 154.08, 154.85, 162.54 (d, J=246), 168.88.

MS (%): 411 (parent+1, 100).

HRMS Calc'd. for $C_{23}H_{24}FN_2O_4$: 411.1720. Found: 411.1747.

EXAMPLE 84

({3-(4-Fluoro-phenyl)-3-[4-(pyridin-4-yloxy)-phenoxy]-propyl}-methyl-amino)-acetic Acid Prepared as in Example 80, in 25% yield, as a foam.

$^{13}$C-NMR (δ, CDCl$_3$): 34.05, 41.79, 53.82, 59.01, 111.93, 116.11 (d, J=22), 117.48, 122.14, 127.84 (d, J=9), 136.13, 147.79, 151.23, 154.97, 162.56 (d, J=246), 165.46, 169.14.

MS (%): 411 (parent+1, 100).

What is claimed is:

1. A compound of the formula I

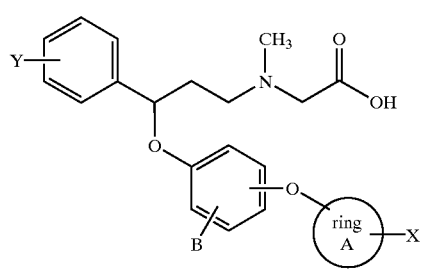

wherein ring A is phenyl or naphthyl

X and Y are each, independently, $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di{$(C_1-C_6)$ alkyl}amino;

B is $(C_1-C_6)$alkyl, $(C_1-C_6)$alkoxy optionally substituted with 1 to 7 fluorine atoms, or halogen;

or a pharmaceutically acceptable salt thereof.

2. A compound according to claim 1, wherein ring A is phenyl.

3. A compound according to claim 2, wherein Y is selected from fluoro, bromo, chloro, methyl, ethyl, methoxy, ethoxy, phenyl, benzyl, and acetyl.

4. A compound according to claim 1, wherein X is 4-trifluoromethyl, 4-methyl, methoxy, phenyl, benzyl, or 4-chloro.

5. A compound having the formula:

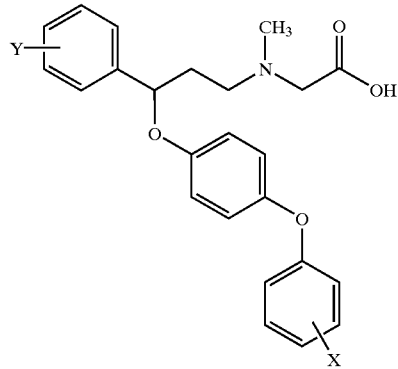

wherein X and Y are each, independently, $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di[$(C_1-C_6)$ alkyl]amino;

or a pharmaceutically acceptable salt thereof.

6. A compound according to claim 5, wherein X is selected from 2-fluoro, 4-fluoro, 4-chloro, trifluoromethyl, acetyl, 2-methyl, 4-methyl, 4-methoxy, phenyl, phenoxy, naphthyl and benzothienyl; or, wherein Y is selected from hydrogen, fluoro, chloro, methyl, and methoxy.

7. A method of treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania, depression associated with bipolar disorder and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia, and other drug-induced and neurodegeneration-based dyskinesias; attention deficit hyperactiyity disorder; cognitive disorders selected from dementias, age-related dementia and senile dementia of the Alzheimer's type; and memory disorders in a mammal, comprising administering to a mammal in need of such treatment an amount of a compound of according to claim 1 that is effective in treating such condition or disorder.

8. A pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia and other drug-induced and neurodegeneration-based dyskinesias; attention deficit hyperactiyity disorder; cognitive disorders selected from dementias, age-related dementia and senile dementia of the Alzheimer's type; and memory disorders in a mammal, comprising an amount of a compound according to claim 1 that is effective in treating such disorder or condition.

9. A method of treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, and movement disorders associated with Parkinson's disease, tardive dyskinesia, and other drug-induced and neurodegeneration-based dyskinesias; attention deficit hyperactiyity disorder; cognitive disorders selected from dementias, age-related dementia, and senile dementia of the Alzheimer's type; and memory disorders in a mammal, including a human, comprising administering to a mammal in need of such treatment a glycine transport inhibiting amount of a compound according to claim 1.

10. A pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia and other drug-induced and neurodegeneration-based dyskinesias; attention deficit hyperactiyity disorder; cognitive disorders selected from dementias, age-related dementia and senile dementia of the Alzheimer's type; and memory disorders in a mammal, including a human, comprising a glycine transport-inhibiting amount of a compound according to claim 1.

* * * * *